(12) United States Patent
Bird

(10) Patent No.: US 8,347,883 B2
(45) Date of Patent: Jan. 8, 2013

(54) MANUAL CONTROLLED BI-PHASIC INTRAPULMONARY PERCUSSIVE VENTILATION AND METHODS

(76) Inventor: Forrest M. Bird, Sandpoint, ID (US)

( * ) Notice: Subject to any disclaimer, the term of this patent is extended or adjusted under 35 U.S.C. 154(b) by 881 days.

(21) Appl. No.: 12/421,669

(22) Filed: Apr. 10, 2009

(65) Prior Publication Data

US 2010/0125227 A1    May 20, 2010

Related U.S. Application Data

(60) Provisional application No. 61/115,151, filed on Nov. 17, 2008.

(51) Int. Cl.
  *A61M 16/00* (2006.01)
  *A61M 16/01* (2006.01)
  *A61M 16/18* (2006.01)

(52) U.S. Cl. ......... 128/203.15; 128/200.21; 128/203.12; 128/204.18; 128/205.18

(58) Field of Classification Search ............. 128/203.12, 128/203.14, 203.15, 204.18, 204.25, 205.18
See application file for complete search history.

(56) References Cited

U.S. PATENT DOCUMENTS

| | | | |
|---|---|---|---|
| 5,165,398 A | 11/1992 | Bird | 128/204.25 |
| 5,862,802 A | 1/1999 | Bird | 128/204.18 |
| 6,581,600 B2 | 6/2003 | Bird | 128/205.24 |
| 6,595,203 B1 | 7/2003 | Bird | 128/200.21 |
| 6,651,658 B1 * | 11/2003 | Hill et al. | 128/204.23 |
| 7,191,780 B2 * | 3/2007 | Faram | 128/204.25 |
| 2007/0256690 A1 * | 11/2007 | Faram | 128/204.21 |
| 2008/0053310 A1 * | 3/2008 | Bliss et al. | 96/115 |

FOREIGN PATENT DOCUMENTS

WO    WO 02/43643 A2    6/2002

OTHER PUBLICATIONS

IPV-1C Institutional Intrapulmonary Percussionator spec., by Percussionaire Oct. 28, 2001. (2 pgs.).
Percussionaire Product sheet, Dec. 12, 2002 (2 pgs.)(shows Impulsator and Phasitron).
Intrapulmonary Percussive Ventilation IPV Discussion paper, copyright Percussionaire 2000. (30 pgs.).
A Manual on VDR—Volumetric Diffusive Respiration (VDR)—The VDR-4 Percussionator for the Most Challenging Patients Requiring Mechanical Cardiopulmonary Care—Percussionaire Corporation, Idaho, Copyright 1996 (75 pgs.).

* cited by examiner

*Primary Examiner* — Loan Thanh
*Assistant Examiner* — Kathryn E Ditmer
(74) *Attorney, Agent, or Firm* — Robert C. Kain, Jr.

(57) ABSTRACT

The method and system ventilates a patient's airway during the inspiratory phase and expiratory phase from a source of pressurized gas, typically from a compressor. The system and method supplies, to the patient airway during the inspiratory phase, a plurality of pulses of small volumes of gas from the gas source, and adds, in succession, pulses of small volumes of gas to provide successively greater volumes of gas successively increasing in pulsatile form the pressure of the gas in the patient's airway. This addition of successively greater volumes of gas serves to provide diffusive ventilation to the patient during the inspiratory phase, and, permits the patient to exhale during the expiratory phase.

44 Claims, 12 Drawing Sheets

Figure 1:
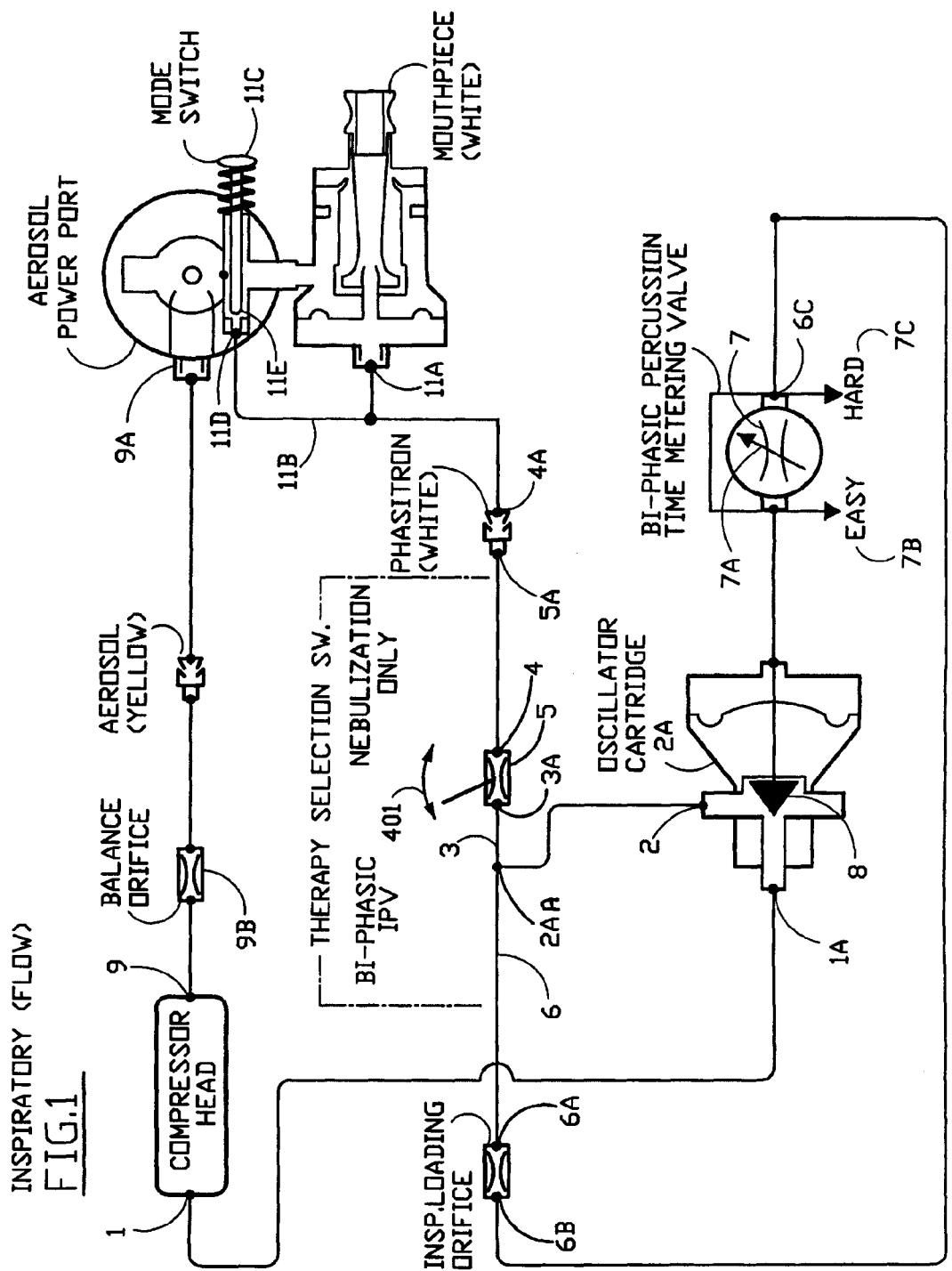

PNEUMATIC CAM FLOW/TIMING CARTRIDGE ASSEMBLY
(in normally open cartridge flow configuration)

Manual created SINUOIDAL BI-phasic Wave Format

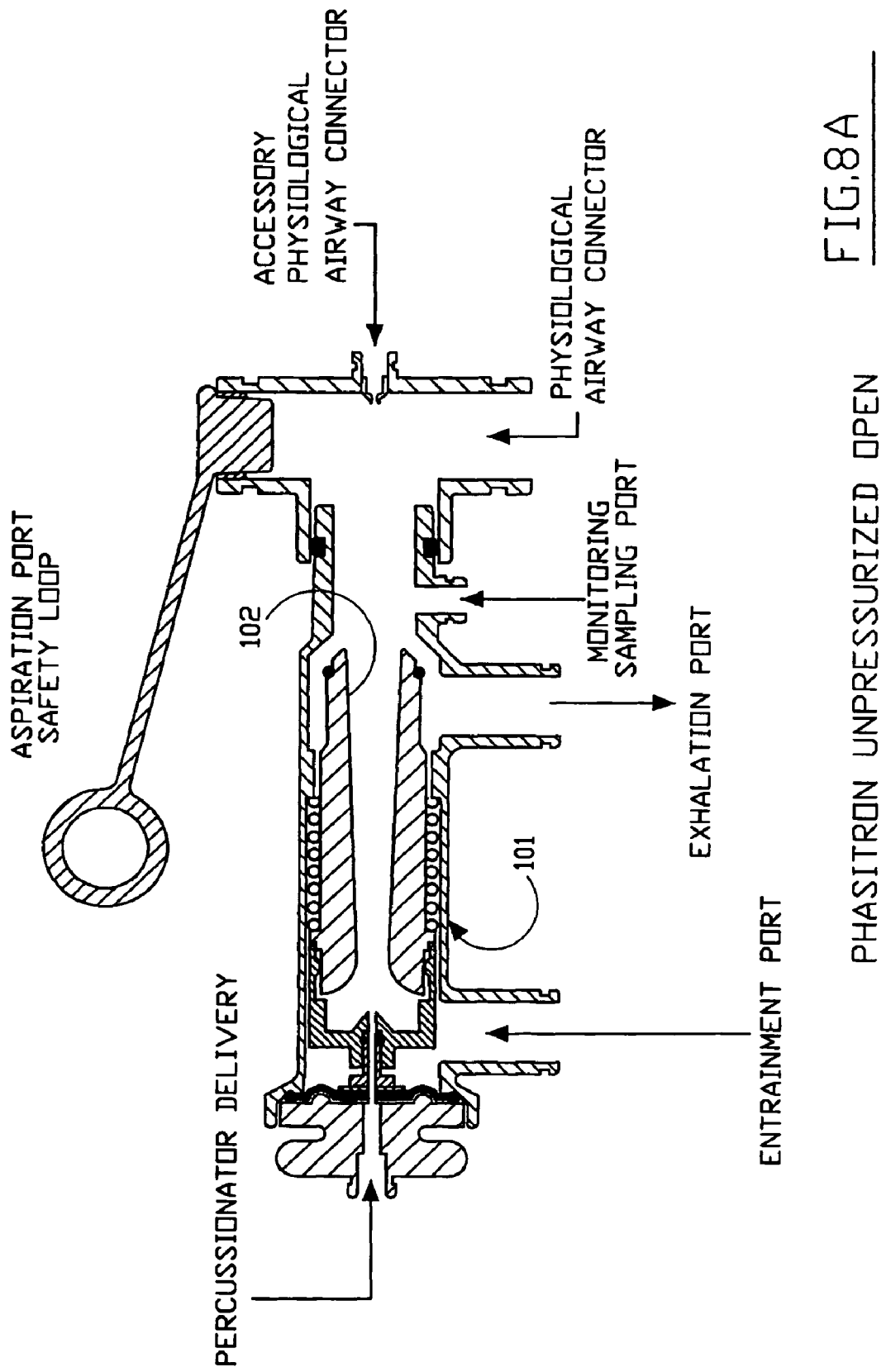

THE DYNAMIC IPV THERAPEUTIC BREATHING CIRCUIT IN CROSS SECTION

MANUAL CONTROLLED BI-PHASIC INTRAPULMONARY PERCUSSIVE VENTILATION AND METHODS

This is a regular patent application based upon provisional patent application Ser. No. 61/115,151, filed Nov. 17, 2008, the contents of which is incorporated herein by reference thereto.

BACKGROUND

The inventor, Dr. Bird, was introduced to fluid dynamics during his pre-WWII aeronautical studies. His WW II airman's pressure breathing device and anti-g suit regulatory developments were followed by his medical education, enabling him to apply his knowledge of fluid dynamics and clinical medicine toward the development of novel fluidic cardiopulmonary support devices.

Dr. Bird has developed several unique methodologies and clinical protocols resulting in four generations of cardiopulmonary recruitment and maintenance medical respirators and Intrapulmonary Percussionators® since the 1950's. These devices have been serially noted to increasingly maintain cardiopulmonary functions in patient's failing all other available continuous mechanical ventilation (CMV) types of pulmonary ventilators.

Many of Dr. Bird's cardiopulmonary support devices employ Dr. Bird's novel fluidic logic without any use of electromotive forces to create functional applications. Bernoullian and Newtonian logic form the basis of Dr. Bird's fluidic concepts. Essentially, a compressed source of a respiratory gas is used as a form of motivational energy source to controllably manipulate the pulmonary structures.

The source of compressed respiratory gases (ranging from 20 to 55 psi.) are converted to the useful mechanical ventilation of the lung by means of a calibrated orificial flow control and the servoing of diaphragms to produce valve openings and active or passive closing etc. See, for example, U.S. Pat. No. 5,862,802, the contents of which are incorporated herein by reference thereto.

Thus, unlike electronically computerized circuitry employing specific "programming logic," the inventor's novel "Fluidic Logic" is all based upon orificial calibration servoing pneumatic uploading and downloading logic cells to regulate functional events. For example: Dr. Bird's conceived Intrapulmonary Percussive Ventilation or IPV® heart lung recruitment and maintenance logic wherein the PERCUSSIONATOR® devices employ total Fluidic Logic, correlated with events occurring within milliseconds, to effectively ventilate the depressed pulmonary structures while providing for a lung protective strategy.

Accordingly, Dr. Bird's conceived Fluidic Logic cardiopulmonary support devices do not employ any computerized or electrical programming of any kind to recruit or maintain depressed heart or lung functions.

The initial "Functional Calibration" enables all therapeutic cardiopulmonary cyclic and static scheduling. It must be remembered mammalian heart and lung functions are basically analog not digital.

OBJECTS AND ADVANTAGES OF THE PRESENT INVENTION

It is an object of the present invention to advance clinical protocols, technological innovations and methodologies, directed toward the enhancement of clinical efficacies of existing clinical administrations, by administering a manual Bi-Phasic™ scheduled Intrapulmonary Percussive Ventilation IPV® protocol in combination with a varying aerosol particulate spectrum and associated sub tidal volume deliveries into the patient's proximal airway, serving to greatly facilitate intuitive clinical therapeutic peripheral lung recruitment and maintenance.

Further objects and advantages of present invention can be found throughout the specifications.

BRIEF DESCRIPTION OF THE DRAWINGS

FIGS. 1 and 2 diagrammatically illustrate the fluid flow and control plan for the Bi-Phasic Intrapulmonary Percussive Ventilation IPV system;

FIGS. 3 and 4 diagrammatically illustrate the hardware and containment bag for the IPV system;

FIG. 5 diagrammatically illustrates the size differential between the new compressor set used in the inventive IPV system compared to a prior art compressor set;

FIG. 6 diagrammatically illustrates the metering valve and oscillator cartridge;

FIG. 7 graphically illustrate the bi-phasic wave;

FIGS. 8A and 8B diagrammatically illustrate the Phasitron valve; and

FIG. 9A diagrammatically illustrates the IPV breathing circuit; and

FIG. 9B is a standard Home Therapy HT™ Impulsator® breathing circuit and

FIG. 9C shows an alternative Phasitron Duo™ breathing head.

SUMMARY

In summary, the present invention is a method and a system for ventilating a patient's airway during the inspiratory phase and expiratory phase from a source of gas under pressure. The system and method supplies, to the patient airway during the inspiratory phase, a plurality of pulses of small volumes of gas from said source of gas, and adds, in succession, pulses of small volumes of gas to provide successively greater volumes of gas successively increasing in pulsatile form the pressure of the gas in the airway of the patient during the inspiratory phase. This addition adds successively greater volumes of gas in the airway of the patient caused solely by the successive addition of the small volumes of gas and serves to provide diffusive ventilation to the patient during the inspiratory phase, and, permits the patient to exhale during the expiratory phase. Further, a smaller compressor set is used and the entire system is containerized in a nylon, shock absorbing travel bag.

It is important for the reader to know about chronic bronchitis and obstructive lung disease (COPD) and how their pulmonary systems can be damaged by incompatible mechanical ventilation of their lungs. This knowledge will advance the understanding of the clinical enhancements of a transportable Intrapulmonary Percussive Ventilation (IPV) treatment apparatus, allowing COPD and other home care patient's to travel, while having near constant access to a light weight travel oriented IPV therapy device enabling their daily multi scheduled lung treatments.

Essentially a pneumatically controlled percussive higher frequency pulsed breathing device was created to enhance a medical treatment protocol called Intrapulmonary Percussive Ventilation IPV® which can be used daily to recruit the diseased peripheral pulmonary bronchioles and alveoli of chronic bronchitis patients, with various partially or totally obstructed bronchioles, without airway damaging hyperinflation. Life supporting bronchioles and their alveoli that remain un-obstructed are called Preferential Airways, which if over-inflated during mechanical lung ventilation can be destroyed by hyperinflational barotraumas.

Typically, barotraumatic lung injuries are caused by lung maintenance ventilators programmed with a mandated volume-pressure limiting means of lung ventilation.

Thus, the novel Home Therapy (HT™) Universal Bi-Phasic™ IPV® IMPULSATOR® delivers institutional quality, percussive higher frequency smaller sub tidal volumes in milliseconds, instead of volume oriented CMV ventilators with lower cycled rates delivering larger intrapulmonary Tidal Volumes into the lungs in seconds. The smaller percussively delivered sub tidal endobronchial volume deliveries in milliseconds provide a Lung Protective Strategy to prevent hyper-inflational barotraumas associated with larger endobronchial Tidal Volumes delivered into the lungs in seconds.

Patients with chronic COPD and acute peripheral lung diseases, have multi degrees of obstructive phenomena within their bronchiolar airways causing major diffuse differences in alveolar gas exchanges. Major components of these bronchiolar airway obstructions are caused by mucosal and sub mucosal edema within the walls of the airways, reducing their internal diameters. Additionally, mucus generated by the Goblet Cells lining the bronchiolar airways, becomes thick and tenacious causing increased airway obstruction because of airway secretion retention. Most important diffuse bronchiolar airways have various degrees of obstruction, while other diffuse bronchiolar airways are un-obstructed.

Generally the diseased bronchiolar airways have mixed degrees of obstruction from open to totally obstructed, the open bronchioles with the least inflow resistance are called "Preferential Airways", become overwhelmed by inflow during CMV ventilatory protocols, as the endobronchial delivery pressures rapidly increase; while attempting to deliver a pre-selected endobronchial Tidal Volume in seconds.

This causes selected hyperinflation of the unobstructed Preferential bronchioles and the pulmonary alveoli they serve, leading to hyperinflational barotraumas to the very dependent lung that is providing life supporting, re-oxygenation functions.

Oxygen can be diffusively delivered into the peripheral pulmonary airways during the inspiratory inflation of the lungs with lesser tidal air exchanges than recruiting and exhaling Carbon Dioxide generated from metabolism, which is delivered into the pulmonary alveoli and must be "pumped" up out of the lungs to ambient by larger tidal breaths.

Dr. Bird's concepts for Intrapulmonary Percussive Ventilation (IPV®) and Volumetric Diffusive Respiration (VDR®) are based upon a higher rate of percussive pulmonary gas exchanges, while maintaining smaller sub tidal volume injections with endobronchial injections timed in milliseconds.

Volume-pressure programmed mechanical lung ventilators deliver large Tidal Volumes "timed in seconds" under available selected peak endobronchial delivery pressures, which are primarily determined by the gross inflow resistances within the pulmonary airways of the lungs. This mechanical ventilatory program timed in seconds produces higher sustained bronchiolar airway pressures, which serve to hyperinflate the Preferential Bronchiolar Airways having the least inflow resistances. This type of volume-pressure mechanical lung ventilation (CMV) can create hyperinflational barotraumas, destroying the most functional lung tissues.

Intrapulmonary Percussive Ventilation (IPV®) of the lungs delivers a constant higher frequency percussive delivery of air-bursts, consisting of small sub tidal volumes into the lungs within milliseconds; without the large lung distending Tidal Volume deliveries of Volume-Pressure limited (CMV) ventilators, which are "delivered in seconds".

Thus IPV® with higher frequency millisecond sub tidal pulmonary ventilation allows the patient to breathe spontaneously "at will" through the percussive sub tidal volume deliveries, without hyperinflation of the bronchiolar "PREFERENTIAL" airways.

Patients with chronic bronchitis and other lung diseases can expand their bronchiolar airways and inflate their pulmonary alveoli at the peak of their spontaneous inhalation. However, the bronchiolar airways that are partially obstructed by bronchiolar wall swelling and retained mucus collapse during early exhalation, trapping gas in their pulmonary alveoli. This causes their bronchiolar airways and their dependent alveoli to be constantly partially inflated during both inhalation and exhalation, this is called "alveolar air trapping." Attached to the outside walls of the partially distended Bronchioles are the Bronchiolar blood vessels that transport blood to nourish the lung structures. In patient's with chronic bronchitis the stretched and narrowed Bronchiolar blood vessels; over time, do not supply sufficient perfusion (blood flow) to the lung structures, causing an increasing ischemia (reduced blood supply) and final necrosis (deterioration) of the peripheral lung structures, similar to the typical end stage lung disease called "Pulmonary Emphysema." Typically Intrapulmonary Percussive Ventilation (IPV®) was conceived and designed to recruit the bronchioles and their dependent alveoli within COPD patient's lungs, who are hospitalized with acute pulmonary infections, creating further encroachment upon their existing chronic lung diseases. Without the lung protective strategies of IPV® certain of this patient population, if placed on volume-pressure oriented mechanical (CMV) ventilators will develop hyperinflational barotrauma. The potential for acute pulmonary infections requiring hospitalization in this COPD patient population is some 2.7 times annually. The rational for the 2.7% rate involvement is based upon the fall cold season, the winter influenza period and a 7 percent chance of patient's becoming infected with summer chest colds.

There are millions of known COPD patients residing within the United States and many more overseas, who employ pharmaceuticals to ameliorate the symptoms of their COPD diseases, without prophylactically addressing the insidious loss of their Bronchiolar (blood supplying) circulations. Thus, over time an ischemic pulmonary Bronchiolar blood supply develops, which can ultimately serve to mandate an untimely Pulmonary Emphysematous death.

Asthmatic patients have acute episodes of peripheral lung obstructions, without the constant hyperinflation of their bronchioles and alveoli. Whereas COPD Patient's with chronic bronchitis have constant unrelenting partial inflation of their bronchioles and their dependent alveoli.

The constant partial inflation of the Bronchioles and their Alveoli of patient's with chronic Bronchitis etc. serves to stretch and narrow their Bronchiolar Blood Vessels, which are attached to the outer walls of the Bronchioles. Thus, the mechanical stretching and narrowing of the Bronchiolar blood vessels of the lung structures, creates an ischemic reduction in perfusive blood flow through the lung tissues.

The diffuse constant partial inflated condition of the peripheral Bronchiolar airways ultimately creates a necrosis leading to end stage lung disease called Pulmonary Emphysema. Thus, the Asthmatic with only infrequent acute bronchiolar and alveolar airway obstructions, without the constant unyielding interference with bronchiolar blood supply, do not loose their Bronchiolar blood supply causing the end stage lung disease called Pulmonary Emphysema. Asthmatics rarely if ever become Emphysemateous.

In the 1980's Dr. Bird had configured a hospital type IPV® Percussionator® with a self-contained air compressor for allowing patients with COPD to take daily hospital quality IPV® treatments within their homes. Since that time thousands of home care Impulsators® have been prescribed world wide for home care IPV® treatments.

The overall results among these COPD patient populations maintaining daily IPV® treatment schedules, have revealed; a very major decrease in acute pulmonary infections, requiring hospitalizations.

IPV® patient's with beginning chronic bronchitis who have not experienced notable Bronchial circulation loss, appear to have minimal if any disease progression if they maintain an exact recommended IPV® treatment schedule. Thus, it reasonably suggests that with daily scheduled IPV® lung recruitments; the patients with beginning Chronic Bronchitis are receiving sufficient remission from Bronchiolar circulatory encroachment, to prevent the expected insidious loss of pulmonary tissue perfusion. In other words, IPV® may therapeutically be preventing the loss of Bronchiolar circulation by multi daily lung recruitment, similar to the Asthmatic patient with extended periods of peripheral airway obstruction remissions.

Many home care patient's using the heavy Percussionaire® Impulsator®, continue to realize the prophylactic clinical efficacy of the IPV® device. Patient suggestions have revealed, that many of these home care IPV® patient's perceive that they are therapeutically confined to their locale because of the weight of their home care therapeutic Impulsator® devices, which do not lend themselves to easy travel. With the number of COPD patient's rapidly increasing, Dr. Bird attempted to conceptively maintain or advance the clinical efficacy of the present heavy IPV® Impulsator®; by conceiving combining methodologies, enabling the application of a novel light weight air compressor with lesser air volumes at lower pressures, to provide for a transportable therapeutic IPV® system. Compare the smaller, lighter compressor set in the foreground of FIG. 5 to the larger compressor set in the background.

Novel methodologies were required to create a percussive IPV® therapeutic endohronchial impaction equal to or better than the existing heavy Impulsator® technology; while employing some one quarter of the current air volume used while maintaining traditional institutional IPV® clinical efficacy, were integrated into novel design. Thus the pneumatic oscillator circuitry and integrated Phasitron® patient interface had to be integrated to maintain the percussive impaction qualities within the cyclic IPV® frequency ranges of the existing heavy Impulsator®.

Design configuration required the innovation of a novel pneumatic oscillation circuitry using a vastly decreased air supply volume, with controlled thermodynamic packaging; to maintain effective environmental compressor cooling within an encapsulating housing; while configuring a condensing temperature drop to cause water condensation beyond the oscillator circuitry.

Figure 3:
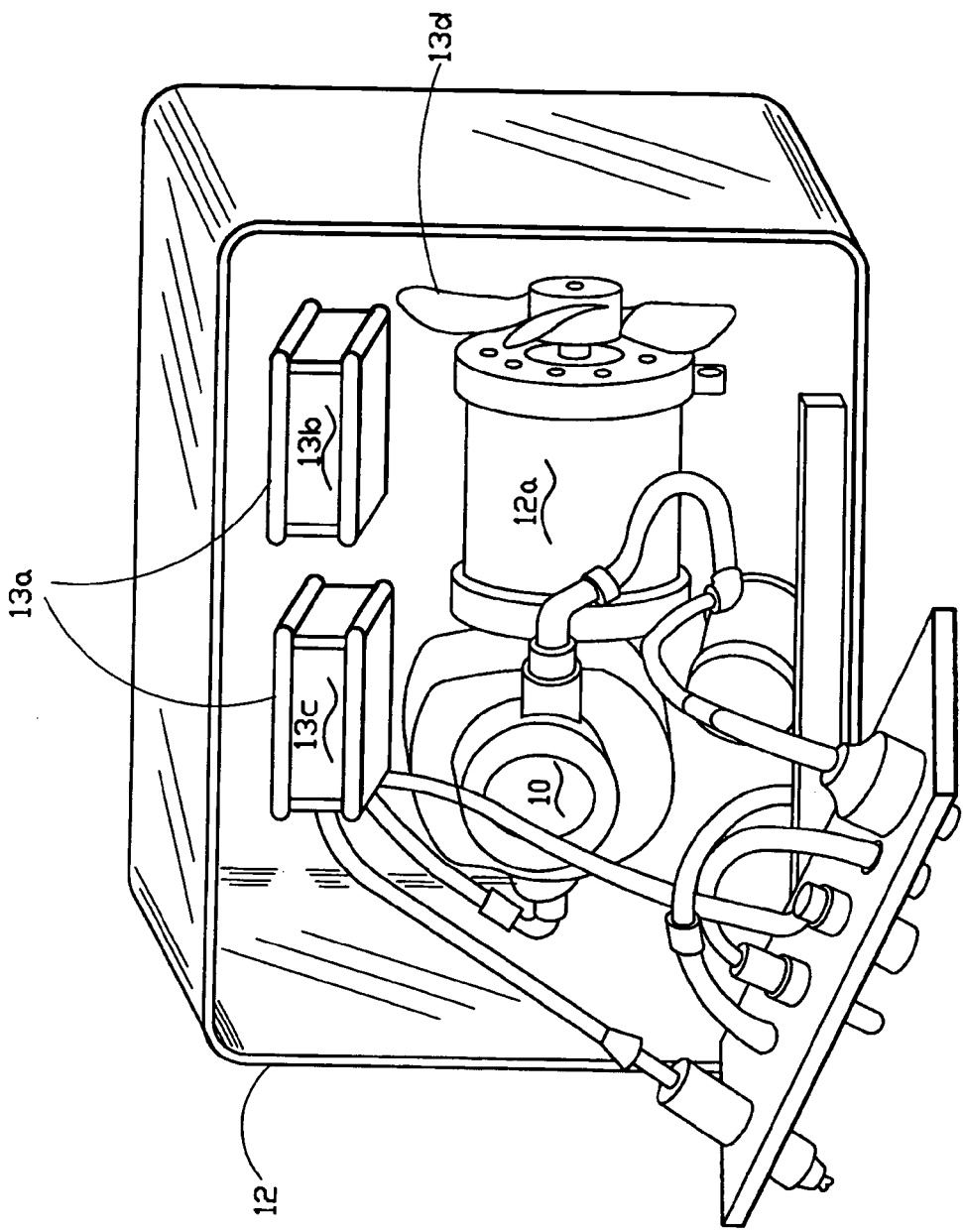

The volume of a deep drawn aluminum encapsulating housing 12, FIG. 3, with a recessed cover to serve as a control panel, with a convective internal ambient air flow through, had to be determined to protect the IPV® apparatus during routine patient travel.

The internal pneumatic oscillator circuitry and the integrated external Phasitron® had to be innovated to provide manual control over cyclic frequency amplitude, with a much reduced, operational compressed air volume.

The following components were removed or significantly replaced from the present heavy Impulsator® design: (a) Replaced the heavy high volume air compressor, with a lighter lower volume air compressor. (b) Removed the operational pressure-volume relieving system. (c) Removed the operational pressure gauge. (d) Removed the proximal airway monitoring system. (e) Removed the oscillatory timing circuit loading check valve. (f) Removed the Phasitron® loading orifice. (g) Removed the external adjustable range calibration orifice.

The Home Therapy HT™ Impulsator®; air compressor oscillation circuit and Phasitron® integration methodology are configured as follows:

1. Air from the compressor head outlet 1, in FIG. 1, is delivered directly into the inlet of the pneumatic oscillator cartridge 1A.

2. Air is directed from the outlet 2 of the Oscillator cartridge 2A into a distribution Tee piece 2AA with design controlled resistances to outflow.

3. One leg of the Tee piece 2AA is directed into the inlet of a two position OFF-ON pneumatic switch 5 with a graded resistance to outflow.

4. The OFF-ON Therapy Selection pneumatic switch 5 has an outlet fitting 4 delivering pulsed gas flows into the inlet of the Phasitron Primary Service socket 4A.

5. Note #1—The outflow resistances between the outlet 2 of the Oscillator cartridge into the Phasitron Secondary Service socket 11A is regulated by design.

Figure 2:
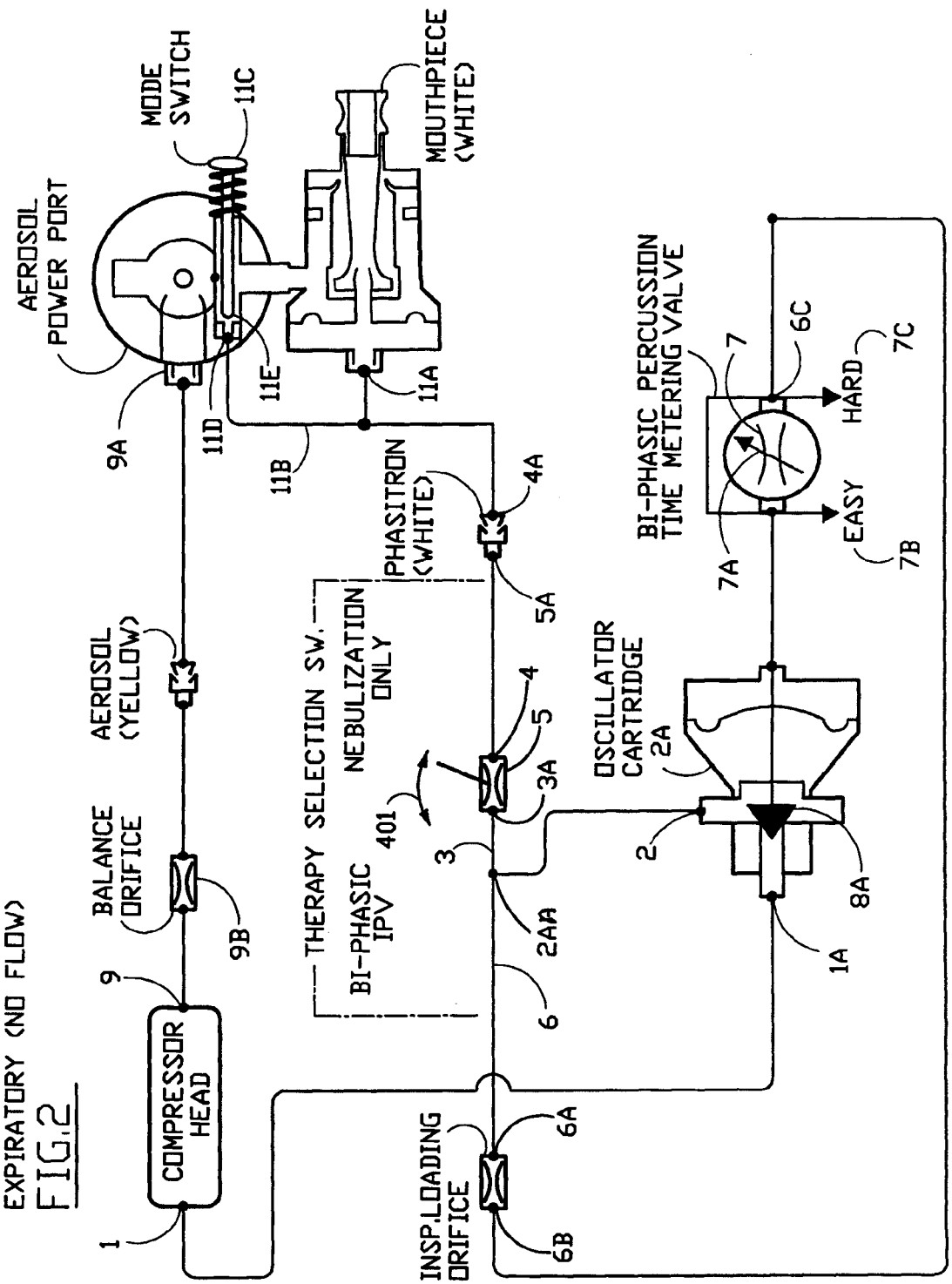

The OFF-ON pneumatic Therapy Selection switch 5, when in the NEBULIZATION ONLY position (see FIG. 2 switch position), interrupts the Oscillator cartridge 2A pulsed gas deliveries to the Phasitron Service socket 11A thereby blocking pulsed air flows to the venturi jet orifice 11A of the Phasitron®. Note #1—The Therapy Selection switch 5 functions are identified by the OFF and ON throws (arrow 401) on the switch stem, which are labeled as follows: In the OFF position, "NEBULIZATION ONLY." See FIG. 2. In the ON position, "Bi-Phasic™ IPV WITH NEBULIZATION." See FIG. 1. Note #2—When the Therapy Selection switch 5 is in the OFF NEBULIZER position, all outflow from the compressor is directed into the nebulization circuit leading to orifice 11A. See labels on switch 4A in FIG. 4.

The opposing leg 6 of the distribution Tee piece 2AA, is directed into the inlet of an inspiratory loading orifice 6A. The outflow from the inspiratory loading orifice 6B is delivered into the common inlet-outlet 6C of the time metering valve 7. Note #1—the inspiratory loading orifice 7D in FIG. 6 limits the rate at which the time metering valve air can upload the oscillator cartridge servoing chamber 7E in FIG. 6 to interrupt oscillator cartridge outflow, essentially controlling the limits of the interrupter valve opening time.

Figure 6:
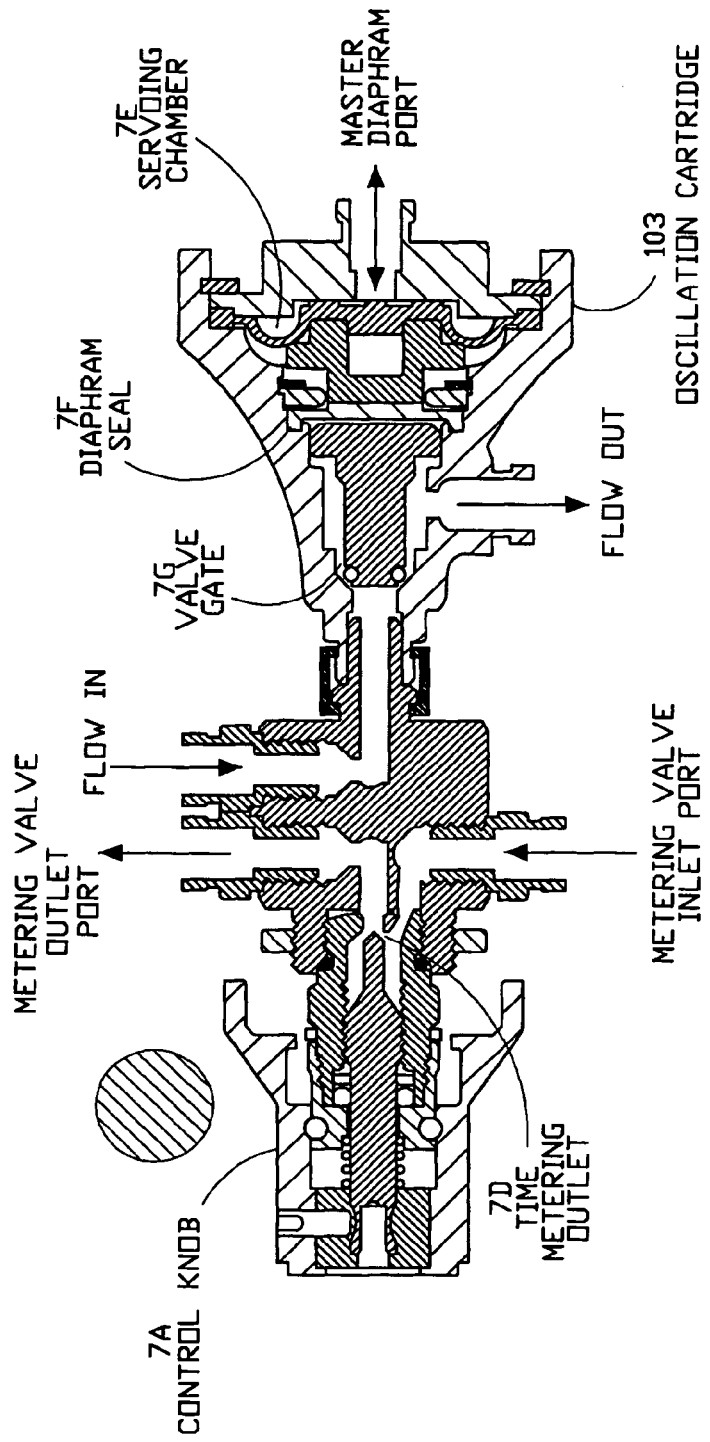

The rotary time metering valve control knob 7A in FIG. 6 with an index arrow, is top identified as "Bi-Phasic™ PERCUSSION" with a 12:00 index labeled AVERAGE.

A left facing PERCUSSION control knob rotation toward EASY 7B in FIG. 1, (see "EASY" label) increases the common up-down loading orifice size decreasing the time required for up-loading and down-loading. A right facing control knob rotation toward HARD marker 7C decreases the common percussion inflow/outflow orifice size increasing the time required for up-loading and down-loading. Note #1—The up-loading pressure within the oscillator timing circuit before flow metering through the inspiratory loading orifice 7D in FIG. 6 would be the same as the venturi jet orifice pressure, which is controlled by the non regulated air compressor operational delivery pressure. Note #2—the percussion time metering orifice 7D in FIG. 6 size will control the rate at which the interrupter cartridge servoing pressure chamber 7E in FIG. 6 is up-loaded, interrupting outflow. It requires a greater servoing pressure chamber pressure rise to close the oscillator cartridge gate 7G in FIG. 6 because of the opening pressure against the diaphragm seal 7F during the period the valve is open. Note #3—The down loading air, out-flowing from the interrupter cartridge valve servoing chamber 7E in FIG. 6 exits to ambient through the un-pressurized Phasitron® sliding venturi tube jet orifice 11A in FIG. 1. Note #4—The rate of air outflow from the servoing chamber 7E (FIG. 6) of the oscillator cartridge 103 in FIG. 6 to re-initiate inspiratory air flow from the oscillator cartridge to the venturi jet orifice, will be longer than the inspiratory flow time because the opening pressure during valve open time, against the oscillator cartridge diaphragm seal 7F (FIG. 6) is absent. Therefore, it will require a greater servoing chamber 7E (FIG. 6) down-loading air volume to allow the valve gate to re-open ending the expiratory no flow time. Note #5—The open-closing time (ratio) of the oscillator cartridge 103, FIG. 6 will automatically vary from near 1 to 1+ at the higher cycling rates to the slower cycling rates of 1 to 3 because of the differentially required valve opening and closing pressures.

Figure 8B:
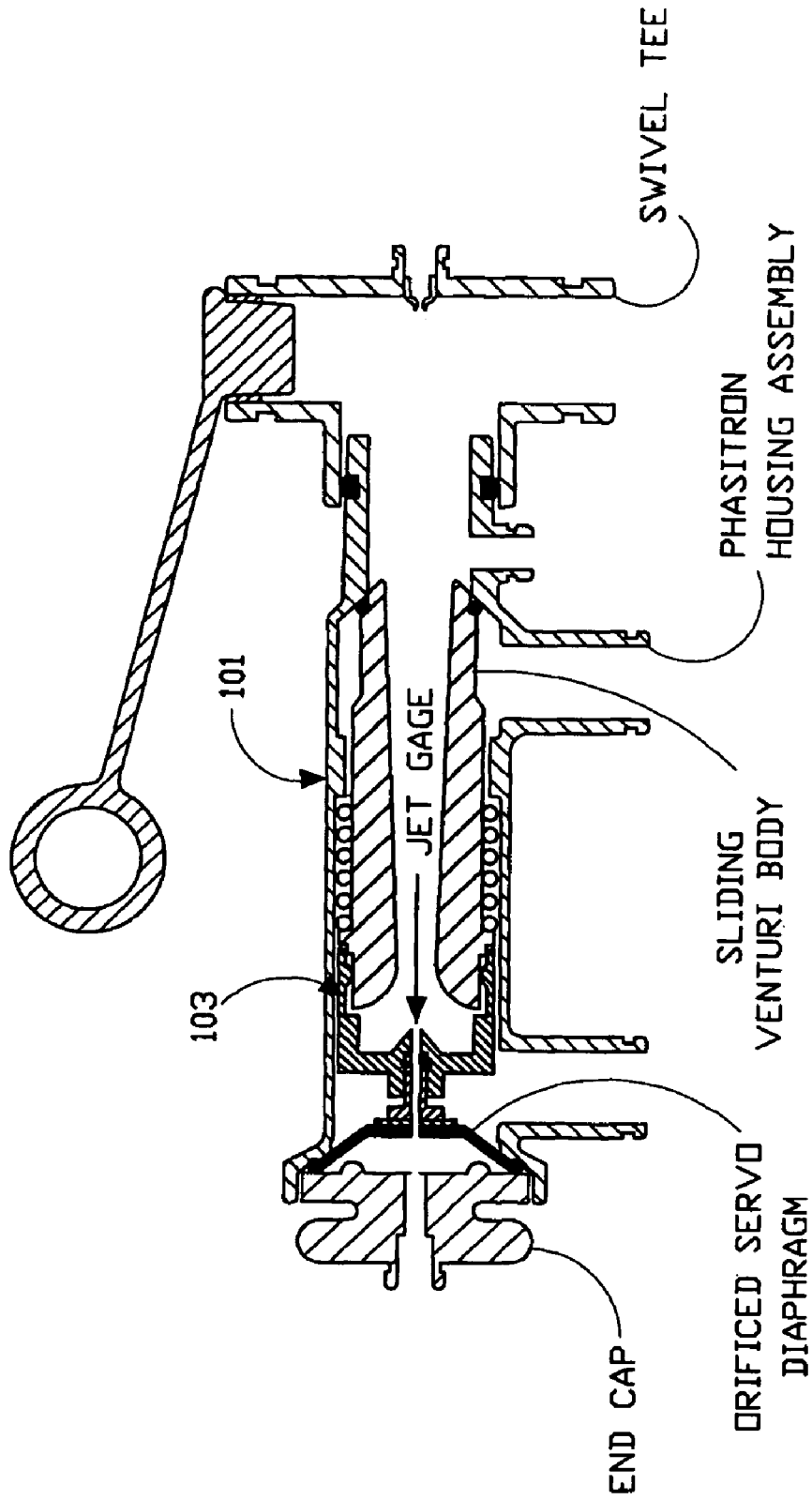

The clean near immediate opening of the interrupter valve gate 7G FIG. 6 within the oscillator cartridge 103 enables a maximum sub tidal volume transfer into the lungs during a selected inspiratory time, for a maximum sub tidal volume to be injected through the Phasitron® into the physiological airways. It follows, that the closing of the interrupter cartridge valve gate 7G must be near instantaneous to allow an immediate opening pressure drop through the Phasitron® to ambient allowing a maximum physiological gas outflow during the allowed expiratory time. Note #1—Any delay in the retraction (opening) of the Phasitron® sliding venturi 102 in FIG. 8A will cause an increase in the residual sub tidal volume of gas remaining within the lungs, creating a partial end expiratory inflation of the pulmonary airways, called a design mandated "Positive End Expiratory Pressure" (PEEP). Designed PEEP can cause the partially inflated pulmonary airways to stretch and narrow the attached Pulmonary and Bronchiolar blood vessels decreasing blood flow through the lungs. This is why the integration of the Oscillator cartridge 103 in FIG. 6 in terms of cyclic flow interruption of the Phasitron 101 in FIGS. 8A, 8B is of such critical importance. Note #2—The percussive sub tidal injection volumes and recovery from the pulmonary airways has been enhanced by a more rapid Phasitron® opening and closing, enabled by decreasing resistance within the Oscillator cartridge timing circuit, to flow gradient reversals.

The constant unregulated air generation of the air compressor is regulated by:
1. First, employing a constant ambient venting of compressed air flowing through the nebulizer jet orifice to ambient preventing a secondary residual compressed air lock up within the pneumatic circuits, which would prevent the compressor from starting against a residual outlet pressure.
2. Second, the Nebulizer is designed to generate aerosol over an expanded inlet pressure range without decreasing the clinical efficacy. Therefore, a balance orifice 9B in FIG. 1 is employed to deliver excess systemic compressed air pressures and their related volumes to the nebulizer jet orifice 9A.
   Note #1—When the oscillatory cartridge 103 in FIG. 6, flow of pulsed air is interrupted by valve gate 7G, the systemic pressure to the nebulizer inlet port 9A in FIG. 1 is increased, increasing the volume of aerosol while limiting the systemic pressure rise.
   Note #2—Thus, this novel means of operational pressure regulation is employed to effectively manage a limited air supply while maintaining selectable percussive sub tidal volume delivery amplitudes associated with the concomitant manufacture and endobronchial delivery of an appropriate aerosol particulate spectrum.

By decreasing the piston stroke volume of the employed compressor; while substantially increasing the compressional stroke volume compression rates, a lesser excess air volume can be design generated, eliminating the mandated venting of compressed air pressure-volumes to ambient. During each compressional stroke volume an "energy surge spike" is created during the overlapping compressional piston strokes. When excess gas volumes are directly vented to ambient by a pressure rise regulator the majority of the "pressure rise energy spikes" are vented to ambient. Note #1—In the Home Therapy HT™ configuration, the "energy surge spikes" created by each compressional piston stroke are directed into the patient's proximal pulmonary airway during sub tidal volume deliveries by the Phasitron® venturi jet orifice 11A in FIG. 1 as well as, through the nebulizer jet orifice 9A serving to internally increase the particulate diffusion during the liquid to particle aerosolization process. Note #2—The sharp microsecond generated "energy spikes" attach themselves to the scheduled sub tidal volumes which serve as transport vehicles for the delivery of the energy spikes endobronchially during sub tidal volume delivery. Note #3—The micro energy spikes transported into the pulmonary airways during sub tidal volume delivery, impact upon the walls of the pulmonary airways decreasing their elastomeric expansional resistance during repetitive sub tidal volume deliveries. Note #4—The micro agitation within the pulmonary airways during each expansive microsecond sub tidal Volume delivery, ceases during the expiratory distal-proximal physiological outflow, providing for a more forceful elastomeric contraction of the pulmonary airways. Note #5—Thus, the more rapid the mechanical expansion and physiological elastomeric contraction of the pulmonary airways during the cyclic sub tidal volume exchange, the greater the directional "vesicular peristalsis augmentation" of the blood and lymph flow though the vessels attached to the exterior walls of the conducting vessels, thus providing for an enhanced intrapulmonary fluid flow.

The lower amplitude percussive sub tidal volume deliveries serve to enhance endobronchial diffusive gas mixing, favoring oxygen uptake. Note #1—A manual controlled mode switch 11C in FIG. 1 allows the patient to intuitively increase convective sub tidal delivery amplitudes, favoring carbon dioxide "wash out" from the lungs. This is periodically accomplished by manually increasing the Phasitron® jet orifice operational pressures.

The following novel manual control over percussive (convective) sub tidal volume amplitude is created as follows:
1. A Tee piece inserted into the end of an approximate 48 inch interfacing tubing bleeds air from the Phasitron Service socket 11A, out through the mode switch orifice 11D to ambient. Line 11B diagrammatically illustrates the lengthy tube. The lengthy tubing (about 48 inches) provides a convenient (remote) inter connection between the Phasitron® service socket 5A and the inlet of the Phasitron® 11A patient interface.
2. A thumb or digit actuated mode switch mechanical plunger 11C can close orifice valve 11D by applying a thumb pressure. The patient controls digit switch 11C with his or her hand and moves rod end 11E into and out of the valve orifice 11D.

3. When the pneumatic mode switch 11C is normally open, a certain amount of the pulsatile. Phasitron® inflow is vented through a calculated orifice size to ambient, decreasing the Phasitron venturi jet pressure. This decreases the amplitude of the percussive sub tidal delivery into the lungs.

When the mode switch orifice 11D is manually closed by switch 11C, the gas flow to the Phasitron® sliding venturi jet orifice 11A is increased, thus increasing the percussive amplitude of the endobronchial sub tidal volume delivery.

Note #1—The above Home Therapy HT™ novelty enables the patient to create a direct intuitive sinusoidal lung recruitment program without the manipulation of the previous remote operational pressure source and/or periodically adjusting the percussive time constants, as was previously required. The heavy Impulsator® mode switch 11C was employed to "interrupt percussive oscillation" while continuing the endobronchial delivery of aerosol generated by the continuous nebulization functions. This leads to patients favoring periods of nebulization at the expense of therapeutic percussive lung recruitment.

Note #2—Another advantage of the present Oscillator-Phasitron integration is the elimination of the IPV® calibration orifice previously controlling the expiratory (down loading) i/e ratio component (inspiratory to expiratory "i:e" ratio) of the out-flowing air from the Oscillator cartridge Servoing Chamber 7E in FIG. 6.

Note #3—When the out-flow orifice of the heavy Impulsator® was obstructed by the breathing head mode switch, oscillation was arrested providing for nebulization only. Additionally, the interfacing tubing interconnecting the removed IPV® calibration orifice with the breathing head mode switch was eliminated in the HT™ design.

Note #4—There are alternate types of mode switches used in two types of Phasitron® breathing heads.

Note #5—The alternate Phasitron® breathing head design employs an ambient vented mode switch orifice venting to ambient. When the mode switch orifice is occluded by the patient's thumb the sub tidal volume amplitude is increased.

The entire self contained Home Therapy HT™ Impulsator® apparatus with the limited pressure-volume air compressor 10 in FIG. 3 is packaged within a deep drawn aluminum housing 12. The compressor 10 is shock mounted in housing 12 to provide isolation and positioning. An inserted top cover panel 12B, see FIG. 4, closes the open top of the housing 12 (FIGS. 3, 4) providing for a labeled control panel 12B for patient control access. Cover top flap 12 BB, FIG. 4, further protects the unit.

Note #1—The environmental compressor thermodynamics within the closed housing are accommodated by the insertion of two fans 13A in FIG. 3 within the aft wall of the deep drawn aluminum housing 12. One fan 13B forces an excess of ambient air into the confines of the housing 12. The other fan 13C evacuates the confines of the housing, with sufficient air exchange to control the temperature drop of heated compressed air within the housing allowing condensational cooling outside the housing to prevent water accumulation within the internal oscillation circuits.

A direct internal compressor driven shaft integrated fan 13D provides for diffuse internal circulation within the housing. The cooling fans employ the same electrical power as the compressor. Compressor 10 is mechanically powered by motor 12A shock mounted in case 12.

Line power is delivered through a lower (grommeted) hole through the left facing side of the housing 12 by an attached and restrained power cord.

Note #1—Adjacent to the power cord grommet are two vertically spaced fuse holders providing split power line protection. The internal wiring meets conventional underwriters standards.

Entrained air is drawn into the compressor through an ambient vented exchangeable filter 17 in FIG. 4 positioned through the top of the control panel 12B.

The entire deep drawn aluminum housing 12 in FIGS. 3, 4, is dropped into a top loading, insulated airline quality nylon container bag 12C in FIG. 4 with a reinforced bottom and semi snug fit. Straps 301, 302 and zipper closures 305 secure the unit in the portable bag 12C. Other closure systems may be used.

Appropriate holes are made through the walls of the nylon container pack 12C to accommodate the aft cooling fans, the left facing side accommodates the electrical power inlet.

The containing transport pack is fastened to the aluminum housing 12 by installed grommet type accommodations as well as, snap type fasteners. In this manner bag 12C is securely mounted on housing 12.

Accommodations for the Home Therapy HT™ Impulsator® accessories are managed as follows:

1. A left facing side pocket 18A contains the power cord in FIG. 4.
2. A front facing compartmented pocket 18B contains the interfacing tubing's and medications etc.
3. A right facing side pocket 18C contains the Phasitron® Breathing head assembly.
4. A left top-side attached zippered nylon fabric open top cover 12 BB with a "zippered inside compartment", provides for the storage of operational instructions etc.

The preceding data describes a novel self contained transportable integrated medical apparatus capable of providing institutional quality IPV® lung recruitment by means of a unique Intrapulmonary Percussive Ventilation (IPV®) Percussionator® housed in a typical transportable airline pack. This device was conceived to allow present or new COPD patients who now have or are considering the heavy home care IPV® Impulsators®, which have been clinically mandated for use at least twice daily; to travel reliably wherever they elect to go with a light weight portable Home Therapy HT™ Impulsator© IPV® therapy device, without fear of being separated from their mandated daily home treatment schedules.

Medically and technically, the preceding information has described novel alterations to the basic IPV® apparatus reducing the volume-pressure requirements for compressed air volumes, enabling the use of a much smaller, lighter and more transportable air compressor while maintaining the current "clinical efficacy of IPV® using the heavy Impulsator®".

Conservation of energy providing for a limited volume of compressed air has been the determining consideration in the conceptual methodology employed to develop a self contained energy efficient transportable IPV® device, while maintaining equal and/or improved clinical efficacy.

The rational for an extremely reliable analog percussive lung ventilatory apparatus for the physiological recruitment of peripheral cardiopulmonary pathophysiological abnormalities makes the present invention, superior to electronically served medical CMV ventilators in terms of functional operational reliability, component simplicity and clinical efficacy while maintaining a lung protective strategy.

Note #1—Most important, the flow rate of sub tidal gases being delivered into the pulmonary airways is continuously, and near instantaneously, varied, by alternating intrapulmonary pressure changes occurring within the lungs, which are regressively transmitted back into the "throat" of a venturi tube 103 in FIG. 8, thus varying the unrestricted entrainment ratios of 1:5 down to obstructive outflows of 1:1+ depending upon intrapulmonary inflational resistances. Thus, the ever-changing intrapulmonary airway resistances to inflow serve to control the instantaneous rate at which the lungs are inflated, providing a physiological control over intrapulmonary distending pressures, designed to prevent hyperinflational barotraumas.

Note #2—Therefore, comparing the novel use of fluidic compressed air energy for the control of depressed cardiopulmonary functions to electronically or mechanically programmed volume-pressure (CMV) ventilators, is like comparing apples to oranges. Specifications for electronic pulmonary ventilators are written for lung ventilatory maintenance and not peripheral lung recruitment as well as "recruitive lung maintenance", while maintaining a lung protective strategy.

Computerization experts are not expected to understand that the use of advanced fluid dynamics employing calibrational logic (without employing computerized programming), in the scheduling of the present innovative pneumatic cardiopulmonary therapeutic devices.

Patho-Physiological Considerations

Intrapulmonary volume trauma, mechanically induced secondary to pulmonary airway hyper-expansional ventilatory CMV scheduling, which can be aggravated by a Positive End Expiratory Pressure (PEEP), has been incriminated by certain physician physiologists, as being the potential cause of alveolar septation. (Null et al. published the following: "Nasal ventilation alters mesenchymal cell turnover and improves alveolartization in preterm lambs." 2008 Aug. 15; 178 (4): 407-18 Epub 2008 Jun. 12. PMD 18556628 (PubMed—indexed for Medicine)) has suggested that premature lamb lungs experiencing periods of some 72 hours of continuous elevated semi static positive airway pressures demonstrated alveolar septation at post.

Illustrations by Null et al. in PEER documental reviews show lung damage caused by a non invasive Continuous Positive Airway Pressure (CPAP) associated with Intermittent Mandatory Ventilation (IMV), could logically be imposing upon Bronchiolar blood flow leading to ischemic alveolar septation (lung damage). Other illustrations by Null et al. show the non-invasive IPV® type lung ventilation without noted septation, when using Oscillatory Percussive Positive Airway Pressure (OD-CPAP) [an IPV® derivative] to simultaneously ventilate the lungs without imposing upon Bronchiolar blood flow.

Positive End Expiratory Pressure (PEEP) advocates, who employ PEEP to increase the Pulmonary Functional Residual Capacities (FRC) of the lungs have challenged the opinions of certain clinician-physiologists who have suggested that PEEP could potentiate Bronchiolar and Alveolar hyper-distention in patients with peripheral lung disease. The inventor became involved with Continuous Minimal Airway Pressures (CPAP) in the early 1970's by conceiving the logic for Demand CPAP, which could maintain a near constant minimal proximal to distal pulmonary positive airway pressures during spontaneous or controlled respiration. He has since created a Demand Oscillatory OD-CPAP concept limiting any potential impact upon the Bronchiolar circulation.

Relatively few pulmonary physicians rationalize that the Intrathoracic Bronchial Circulation, if challenged during long term mechanical ventilation, by a constant elevated expiratory baseline, can create a peripheral airway and alveolar ischemia, ultimately terminating in necrotic tissue. Many clinicians have become so dependent upon PEEP in the apneic patient and CPAP in the patient without peripheral airway disease (in the spontaneous breathing patient in terms of PaO2 enhancement) that the basic pathophysiology of COPD (chronic obstructive peripheral lung disease) may become shaded.

Clinical alveolar septation can be demonstrated in animal experiments when a long term continuous proximal-distal airway pressure gradient is maintained with or without limited mandatory intrapulmonary tidal exchange, during spontaneous respiration. This observation may in part demonstrate that without an adequate percussive physiological or mechanical enhancement, to the three intrathoracic circulations by physiological or mechanical means, such as induced "Pulmonary Vesicular Peristalsis" the bronchial circulation is continuously impaired by partially inflated peripheral airways and their alveoli, serving to stretch and partially narrow the caliber of the Bronchial circulatory vessels, thus creating a long term ischemic trend.

The inventor's concept of Intrapulmonary Percussive Ventilation IPV® with associated mechanically created "Intrapulmonary Vesicular Peristalsis", has served to enhance intrathoracic directional vesicular blood and lymph flow.

The IPV® concept was directed toward providing a recruiting percussive sub tidal gas exchange into and within the respiratory bronchioles and associated alveolar structures, while providing for a lung protective strategy. Thus the inventor's concept was to mechanically provide for peripheral lung recruitment while minimizing the potential for induced barotrauma.

Equally important is the production of a uni-directional "Vesicular Peristalsis" within the three intrathoracic circulations, namely the Bronchial, Pulmonary and Lymph circulations. "Vesicular Peristalsis" is dependent upon having the proximal airway vented without restriction, to ambient during the repetitive milli-second expiratory phases of sub tidal endobronchial gas exchange.

Before the near collapse of the supporting positive bronchiolar airway pressures and before the peripherally congested pulmonary airways depressurize and contract toward their obstructive positions, the next controlled percussive inspiratory sub tidal volume is mechanically delivered endobronchially, to re-inflate the contracting bronchiolar airways and deflating pulmonary alveoli. Therefore, the entire tracheobronchial tree receives continuous peristaltic directional pulsatile stroking waves from the trachea into the peripheral bronchiolar airways, during programmed sub tidal volume delivery intervals. As the pulmonary airways are mechanically caused to cyclically contract and expand, the attached vessels of all three intrathoracic circulations are repeatedly peristaltically compressed and released, during the cyclic expansion and contraction of the pulmonary airways to which they are attached.

Thus, the inventor's concept of Intrapulmonary Percussive Ventilation IPV® serves as a lung recruitment means by the percussive intrapulmonary gas mixing and gas exchange as well as, enhancing the directional vesicular flow of fluids flowing through the three intrathoracic circulations, thus enhancing a mechanically induced "Vesicular Peristalsis".

Another PEER supporting article is by Schiller, (Effect of positive end expiratory pressure and tidal volume on lung injury induced by alveolar instability, Critical Care 2007, 11:R20 et al., in Critical. Care Medicine, 2001; 29:1049) discusses and shows the acute respiratory distress syndrome ("ARDS") lung (at 100 magnification), is associated with lowered surface tensions, mucosal and sub mucosal edema, retained endobronchial secretions and bronchiolar spasm, which can all lead to alveolar over distension in the destabilized ARDS lung, secondary to "Preferential Airway" related alveolar hyper distension associated with volume-pressure oriented (CMV) lung maintenance ventilators.

Thus, it may be further illustrated that Preferential hyper volume induced pulmonary barotraumas may well be created by volume-pressure (CMV) limiting techniques in patients with obstructive peripheral lung encroachment (disease) however caused. (Gary Neiman et al., Upstate Medical Center, New York University published—"Injurious mechanical ventilation in the normal lung causes a progressive pathologic change in dynamic alveolar mechanics." Critical Care 2007: R64).

Gary Nieman's clinical finding have again shown by using unique living mammalian lung models volume-pressure limited continuous mechanical pulmonary ventilation (CMV) is tolerated in near normal pulmonary structures (lungs). However, when the peripheral pulmonary airways (bronchioles etc.) serving alveolar structures become unevenly diffusely encroached upon by mucosal and sub mucosal edema, retained endobronchial secretions, bronchiolar spasm as well as other factors, the three intrathoracic circulations can be progressively encroached upon leading to ischemia and ultimately non reversible necrotic alterations such as various forms of respiratory distress syndromes and end stage diffuse obstructive pulmonary emphysema.

While current medical research continues to support the clinical efficacy of Intrapulmonary Percussive Ventilation IPV® advancing research reveals that technological novelty can further facilitate the clinical efficacy of the Intrapulmonary Percussive Ventilation IPV® and Volumetric Diffusive Respiration VDR® protocols, by applying innovative rationales.

Primary Revelations, Supporting Technological and Clinical Data

Certain functional, therapeutic, administering protocols, and methods are set fourth in: (a) Ventilator Having an Oscillatory Inspiration Phase and Method, U.S. Pat. No. 5,862,802, the contents of which is incorporated herein by reference thereto; (b) Apparatus for Administering Intermittent Percussive Ventilation and Unitary Breathing Head Assembly for Use Therein, U.S. Pat. No. 6,595,203, the contents of which is incorporated herein by reference thereto; (c) Interface Apparatus and Combination and Method for use with a continuous Volume-Pressure (CMV) ventilator and an Intrapulmonary Percussive Ventilator and Combination thereof and the IPV®-VDR® associated embodiments set forth in U.S. Pat. No. 6,581,600 B2 the contents of these U.S. patents are incorporated herein by reference thereto.

Figure 4:
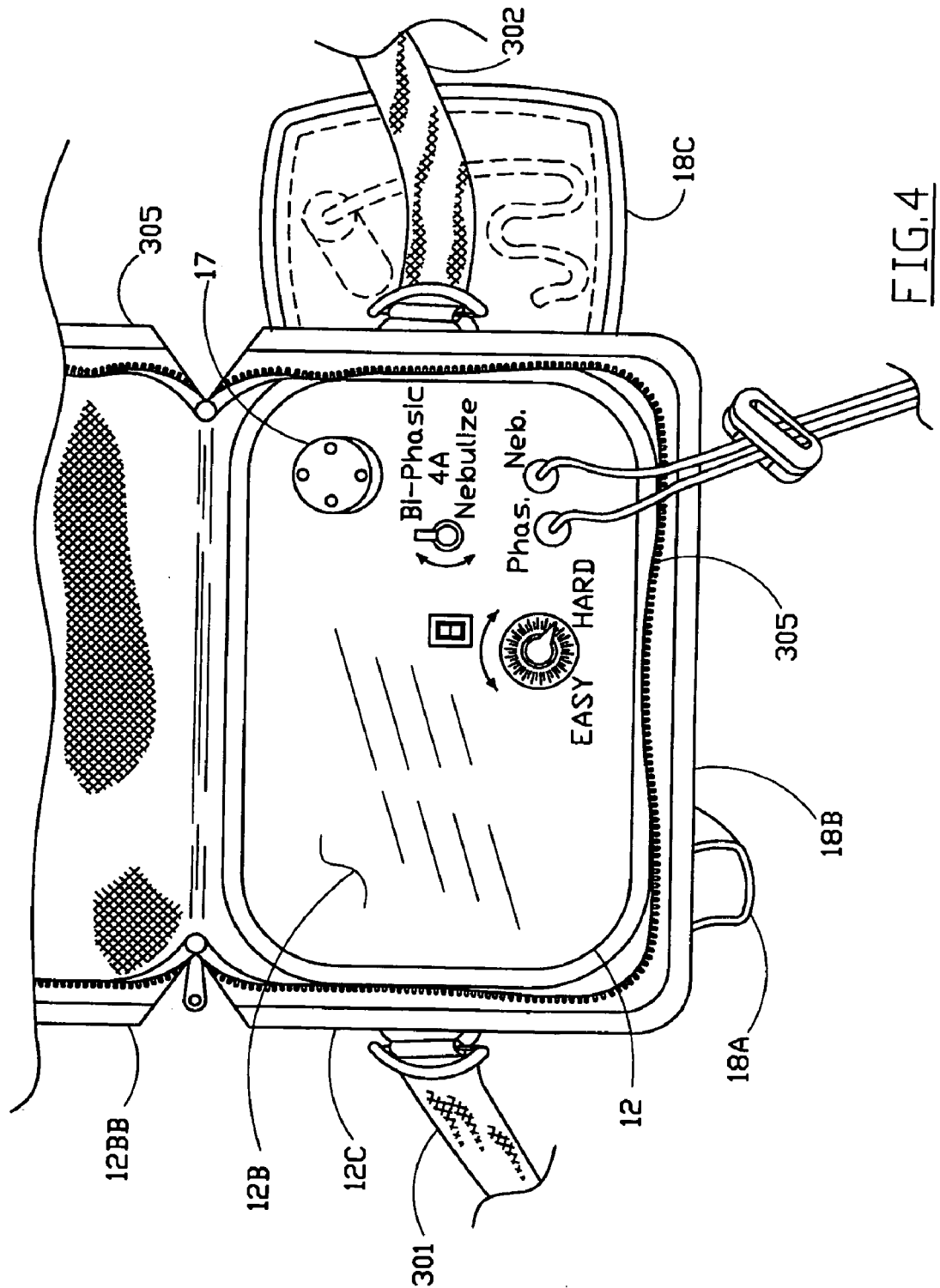

The current Intrapulmonary Percussive Ventilation IPV® heavy Impulsator® is semi portable and has a self-contained IPV® Percussionator® device with an internal high volume/pressure air compressor 10 weighing about 18 pounds (compressor-motor unit) see FIG. 4, background compressor set, capable of generating some 90 psi. The overcapacity air-flow of the heavy Impulsator® is regulated with a pressure reduction regulator monitored by an operational pressure gauge. Normal selected operational pressures are from 25 to 55 psig. The higher generated flow pressures are vented to ambient by a pneumatic pressure-regulating device.

The definition of an intra pulmonary induced "Sub tidal volume exchange" is the cyclic percussive pulmonary airway injection of an air volume, which is less than the total patient's "Physiological Dead Space" (where a blood gas exchange interface does not exist).

In order to obtain a sharp percussive impulse during sub tidal volume injection, the selected injection (the Ram Pressure) must be adequately maintained.

The generation and endobronchial delivery of aerosol particles (nebulization) is continuous during percussive higher frequency oscillation or spontaneous respiration provided by the compressed air output flow/pressure, which can be regulated by restrictive multi orifice integration.

Intrapulmonary percussion is generated, by the controlled cyclic (full opening and closing) of a normally open pneumatic oscillatory flow/timing cartridge timed in milliseconds. The selected regulated operational pressure during flow demand is generated by a high rpm stroke volume delivery (some 3500 rpm) with a calculated overlapping piston stroke volume sufficient to provide for the mandated flow/pressure demand of the IPV® apparatus. The overlapping pulsatile cumulative compressor stroke volumes create an "Energy Spike" during each stroke, during the repetitive flow/pressure generated volume accumulation, which is super-imposed upon each sub tidal endobronchial delivery. Compressor created air inflow is internally interrupted by a flow interrupter Oscillator cartridge, oscillating at selected cycling rates (in milliseconds), usually from about 100 to 500 cycles per minute.

Cyclic flow interruptions are designed to automatically produce optimal near instantaneous opening and closing, inspiratory-to-expiratory flow gradients with "i/e" ratios of from 1:1+ at the higher selected frequencies down to 1:3 at the lower scheduled frequency selections, which are calibrated to maintain the patient's near normal functional residual capacity (FRC).

FIGS. 8A, 8B show a physical-physiological proximal airway-interfacing device called a PHASITRON® 101 which serves as a percussive proximal airway located injector/exhalation valve, essentially serving as a pulmonary airway interfacing respirator. The PHASITRON® airway-interfacing device contains a sliding venturi tube-jet assembly 102 for endobronchial sub tidal air injection, as well as expiratory ambient venting, of the entire proximal pulmonary airways. The oscillator cartridge 103 delivers percussive gas impulses (in milliseconds) into the venturi jet inlet orifice 11A in FIG. 1 of the Phasitron® (airway-interfacing device). The opening and closing i/e ratios of the Oscillator cartridge 103 in FIG. 6 are controlled by pressure differentials created by servoing pressures across a configured diaphragm seal 7F.

The Closed (Pressurized) Phasitron® sliding venturi 103 in FIG. 8B shows a physical-physiological proximal airway interfacing device which is servoed by the Oscillator cartridge 103 in FIG. 6 which delivers percussive bursts of air (in milliseconds) into the venturi jet orifice inlet 11A of FIG. 1 of the Phasitron® (airway-interfacing device). The opening and closing i/e ratios of the oscillator cartridge 103 in FIG. 6 are controlled by designed pressure differentials.

A pneumatic digit (finger-thumb) controlled manually operated "normally open" mode switch 11C in FIG. 1 and mode switch orifice 11D, are located atop the nebulizer. When the digitally operated mode switch 11C is not depressed, (venting the mode switch orifice to ambient) a component of the air routed to the Phasitron® venturi jet orifice is bled to ambient, through the mode switch orifice 11D, creating a flow-pressure decreases to the venturi and nebulizer jet orifices. Thus, causing the amplitude of the scheduled sub tidal volume delivery to be decreased. When the mode switch button 11C is manually depressed, arresting the ambient air bleed, the pressure to the venturi jet and nebulizer orifices are increased, which increases the amplitude of the endobronchial sub tidal volume deliveries. The mouthpiece outlet of the Phasitron® airway-interfacing device must be sealed by the patient's lips for repetitive, percussive sub tidal air volumes to be injected into the airways of the lungs. Other means to connect the Phasitron® outlet to the patient airways such as masks and indwelling airway tubes can be electively used.

Figure 7:
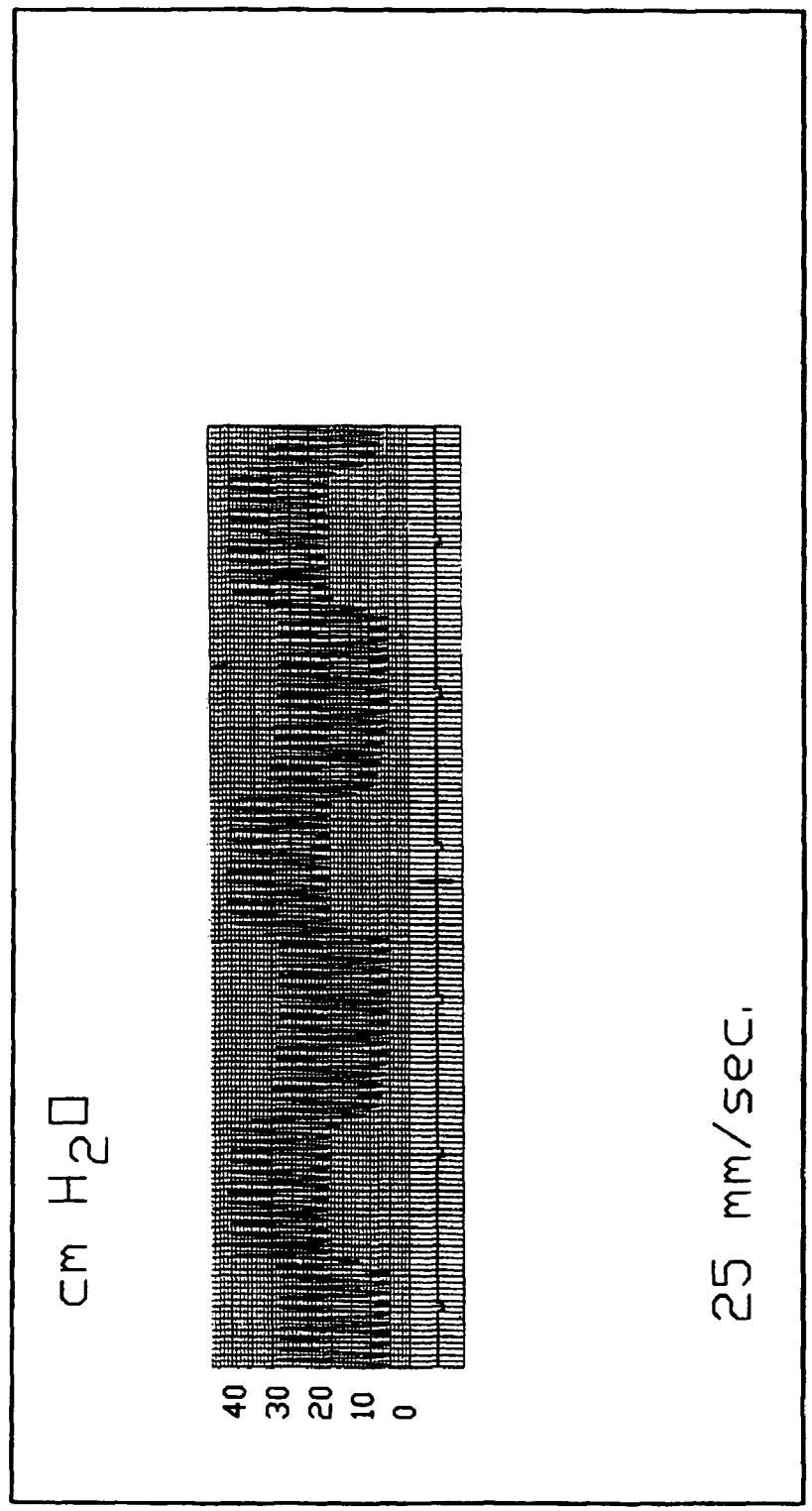

The waveform FIG. 7 demonstrates that a sinusoidal waveformat can be created when the patient systematically depresses and releases the mode switch, creating a Bi-Phasic™ sinusoidal high-low amplitude percussive oscillation, during the delivery of the selected periodic sub tidal endobronchial deliveries. If the patient so elects, they can spontaneously breathe though the scheduled percussive oscillatory program. Spontaneous breathing would decrease the peak oscillatory pressure rise during inhalation and increase the peak oscillatory pressure rise during exhalation, within the limits of venturi jet orifice inflows.

The percussive near instantaneous opening and closing of the oscillator (flow-timing) cartridge 103 in FIG. 6 is a factor of design. The percussive oscillatory cartridge opening— (flow) and closing—(no flow) time are controlled by reversing flow through the common up-loading and down-loading time metering valve inlet orifice 6C in FIG. 1. The time metering valve orifice 7D with calibrated rotation is labeled from EASY at mark 7B to HARD at mark 7C.

The Intrapulmonary Percussive Ventilation IPV® concept step inflates the lungs to a full ambient venturi flow/pressure clutching, called "oscillatory equilibrium". See waveform, FIG. 7.

The oscillatory pressure rise (amplitude) is determined by patient activation of the mode switch 11C. The clinical management of obstructive pulmonary disease is classically directed toward the recruitment and maintenance of the bronchiolar airway patency (size), which is limited by mucosal and sub mucosal edema as well as, retained endobronchial secretions and smooth muscle spasm, diffusely imposing upon alveolar gas exchange.

Patients using the heavy Impulsator® on a daily schedule for lung recruitment could consider the light-weight Home Therapy HT™ Impulsator® with the novel patient controlled Bi-Phasic™ therapeutic means, if they desire to travel while maintaining clinical treatment efficacy. Home patients who depend upon their heavy IPV® Impulsator must consider their life style. If they feel "tied down" and have the desire to travel the Home Therapy HT™ Impulsator may be an ideal choice.

Some of the therapeutic treatment mandates of the heavy Percussionator® generally favoring the novelization employed in the light-weight Impulsator® are:
1. The existing 25+ pound weight of the heavy Impulsator® may require logistical assistance to the semi invalid patient.
2. Setting up the existing (airway-interfacing device) Phasitron® breathing head with the four (4) interfacing tubing requirements as opposed to two with the Home Therapy HT™ Impulsator design.
3. Pulmonary disease treatment protocols should consider the existing self contained heavy Impulsator® in comparison to the light weight Home Therapy HT™ Impulsator® with the novel patient controlled Bi-Phasic™ therapeutic means.
4. Selecting the proper operating pressure for patient size and patho-physiology.
5. Selecting the recommended percussion cycling frequency.
6. Teaching the patient to maintain a lip seal around the mouth-piece without nasal venting.
7. Establishing a peripheral pulmonary airway mobilization program followed by alternating lung recruitment scheduling.
8. Instructing the patient to manipulate cycling frequency and impaction forces to ventilate, mobilize and then raise their retained endobronchial secretions, while delivering medications to reduce the intra airway swelling and enhance secretion mobilization, by recognizing the manual manipulation of operational pressures, percussive frequency and percussive sub tidal delivery forces.
9. Teaching the patient how to program the operational pressure selection and monitor the operational pressure gauge.
10. Teaching the patient how to interpolate the proximal airway pressure manometer.
11. The patient can be expected to deviate from effective therapeutic percussive therapy protocols (not following prescribed orders) by selecting an operational pressure below clinical effective peripheral airway impaction pressures.

The patient must manually select NEBULIZATION therapy without lung recruiting sub tidal volume deliveries. This feature favors the patient maintaining the more effective Bi-phasic™ lung recruitment schedules.

Improved Clinical Efficiency provided by the Home Therapy HT™ Impulsator

The following data highlights areas where the application of the novel Home Therapy HT™ Impulsator® for travel, with technology directed toward actually improving overall clinical IPV® efficiency, may present a greater patient intuitiveness.
1. The present heavy IMPULSATOR®, weighing over some 25 pounds, may be difficult for a semi invalid patient to carry during transport, eighteen pounds of which is the weight of the air compressor.
2. If the device is dropped, the heavy compressor acts as an internal battering ram to dislocate the compressor from the shock mounting case attachments. Additionally, if it were to fall upon a patient's legs, toes etc. serious injury could result.
3. The heavy Impulsator® mandates a high volume compressor capable of maintaining selectable operational pressures of up to 55 psi to maintain the selected repetitive percussive sub tidal endobronchial volume impulse.
4. The heavy Impulsator® air compressor is noisy (like a vacuum cleaner). In order to limit compressional noise levels for appreciable noise reduction, while providing for adequate compressor head surface fan cooling, the present heavy Impulsator® housing would have to be considerably enlarged, further limiting logistics.
5. The current heavy Impulsator® device allows the patient too much access to therapeutic programming enabling deviation from the most effective clinical protocols, which may be based upon lack of clinical knowledge by those who prescribe the therapy to the patient.

The Air Compressor System

Figure 5:
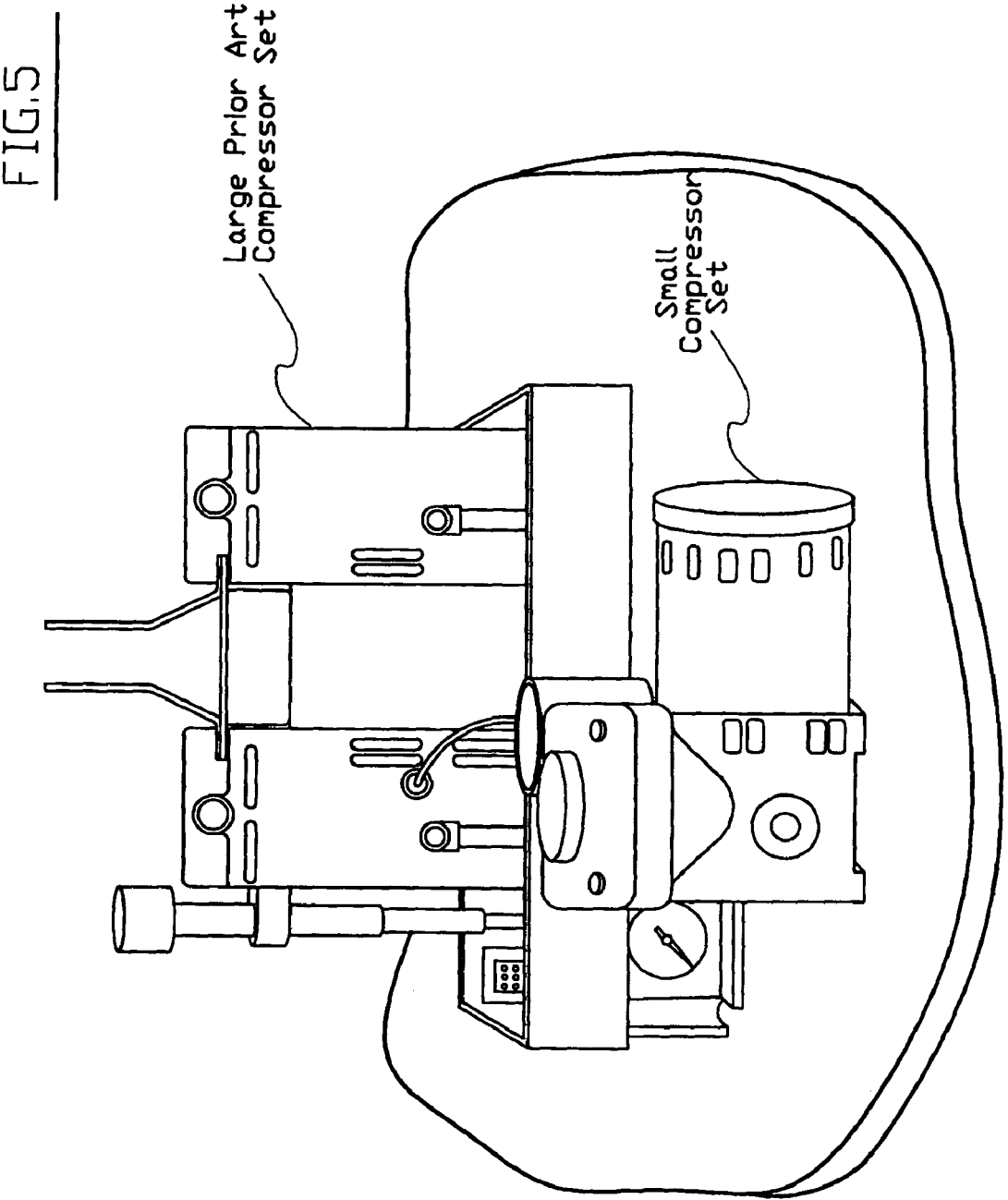

Resolving certain mechanical and clinical limitations of the current logistical state of the art must first address the air compressor. Considerations directed toward increased levels of clinical efficacy and operational convenience and intuitiveness may consider the following:

1. Selecting an appropriate air compressor must consider; air output, weight, operational power limitations, noise, compressional water condensation, operational cooling, oscillatory impaction associated with instantaneous demand pressure drop, operational reliability and functional longevity.
2. The novel methodology addressing the compressed air management system and operational means, can reduce the compressor mass to less than about one fourth of the present bulk and weight with less compressional heating, with a major operational sound reduction. FIG. 5 shows the smaller compressor set used in the present invention in the fore ground and the larger prior art compressor set behind the smaller set.
3. The selection of an air compressor with a smaller diameter piston with less volume than the current larger piston air compressors, capable of developing an equal or near equal operational demand flow/pressure generation through an increase in compressional stroke rates. This was accomplished by increasing the rate of compressive strokes to some two to three times the current compressive delivery rates.
3. By limiting plumbing flow obstructions (restrictions) such as flow through acute angled fittings and restrictive tubing, a pressure reduction regulator, ON/OFF switch etc.

The Home Therapy HT™ Impulsator® has two separate interfacing oscillator and nebulizer outlet Service sockets appropriately labeled for the user as BI-PHASIC and NEBULIZER. These labels are adjacent service ports in FIG. 4.

The first compressor head outlet fitting 1 directs outflow directly into the Oscillator cartridge inlet 1A. The second compressor head outlet fitting 9 provides for the continuous flow-pressure demand of the nebulizer through a flow-pressure balance orifice 9B additionally serving to balance the preferential flow into the Phasitron® venturi jet orifice.

1. The total air generating output of the dynamic compressor must be balanced against:

the Phasitron® venturi jet and the nebulizer jet orifices, to provide for the rapid systemic pressure changes when the amplitude of oscillation is changed by the patient.

2. The two flow balancing orifices 9A of the nebulizer and 11A of the Phasitron® venturi jet orifices are calibrated such that a selected percussive cycling pressure impulse produces sufficient preferential percussive impaction to recruit congested peripheral pulmonary airways. Peripheral pulmonary airway flow must be concomitantly aerosolized with a controlled nebulizer particulate generation.
3. Flow-pressure demands for both functions must be accommodated within the maximum output flow-pressure limits of the compressor without a dedicated reservoir.
4. Venting of the compressor head nebulizer outlet to ambient through the nebulizer jet orifice 9A will immediately release residual head pressures to ambient thus negating attempted starting against a compressed air load.
5. A leg of a Tee piece directs unrestricted flow from the outlet of the oscillator flow interrupter cartridge 2A through a Therapy Selection switch 5 to the orifice inlet 11A of the Phasitron® venturi jet orifice. Switch 5 is user-labeled "Bi-Phasic IPV" and, in its opposite position, "NEBULIZATION ONLY." See FIG. 1 and FIG. 4.
2. A lengthy tubing (about 48 inches) provides a convenience (remote) inter connection between the Phasitron® service socket 5A and the inlet of the Phasitron® 11A patient interface.

A pneumatic flow timing valve assembly, controls the timing of the pulsatile systemic air-flows forming an oscillatory circuit with adjustable cycling rates. This is accomplished by delivering oscillator cartridge outlet air 2 through a Therapy Selection switch 5, through a Phasitron® Service socket 5A then delivering the pulsatile sub tidal air flows through an extended tubing to the Phasitron jet orifice 11A.

The uploading of the oscillator cartridge 2A, see also 103 in FIG. 6, servoing chamber 7E in FIG. 6 pressurizes the oscillator servo diaphragm. Upon pressurization the diaphragm moves a valve stem forward effectively closing the valve gate 7G producing a "no flow" condition.

Following servo chamber uploading with associated timing circuit flow interruption, the diaphragm servoing chamber down loads reciprocally through the common up-down loading time metering valve orifice 7, depressurizing the diaphragm thus causing the re-opening of the oscillator cartridge valve 8 in FIG. 1.

The higher mandated reciprocal uploading pressure than downloading pressure against the common time metering valve orifice 6C, creates a shorter up loading (valve open time) than down loading valve closed time, automatically programming a neutral or longer valve closed time. This is called the opening-closing pressure differential or i/e ratio.

Upon valve closure "no flow" the reversing down loading air flows to ambient through the common up and down loading and unloading time orifice, creating an equal to or longer down loading (valve closing) time than up loading time (because of the differential up and down loading pressures, mandating a longer "no flow" (expiratory) time.

Higher sub tidal cycling rates are created by selecting a larger common orifice causing a more rapid up loading as well as proportionately longer down loading time. The opposite is obtained when a smaller common orifice creates smaller sub tidal cycling rates. The differential in a constant uploading pressure to a decaying down loading pressure mandates a neutral or positive i/e ratio. Thus, because of the larger common selected orifice at higher cycling rates, as opposed to a smaller common selected orifice at lower cycling rates the i/e ratios remain neutral or positive.

Following servo chamber bleed down causing oscillator cartridge valve opening 8 in FIG. 1 and the delivery of uploading air into the inlet of the time metering valve as well as the inlet of the Phasitron® venturi jet orifice 11A, up-loading begins. Because of the pressure against the diaphragm seal 7F in FIG. 6 during valve opening, it will require a greater uploading pressure to close the valve than required for down loading. Thus down loading will require a longer bleed down time, increasing the expiratory time (valve closed) as compared to inspiratory time (valve open). The common time metering valve orifice 6C in FIG. 1 primarily down-loads through the inspiratory loading orifice (when the therapy selection switch is in the Bi-phasic IPV position) through the cyclically deactivated Phasitron® venturi jet orifice.

The remote patient operated mode switch 11C controls the amplitude of a selected percussive oscillatory cycling frequency. With the mode switch not depressed part of the periodic inspiratory flow directed into the Phasitron venturi jet orifice is vented to ambient, decreasing the amplitude of the selected sub tidal volume injection. When the patient depresses the mode switch button 11C, the ambient bleed of part of the venturi jet flow is interrupted causing a pressure rise in the Phasitron® venturi jet and nebulizer orifices. This increases the amplitude of sub tidal volume delivery.

When the therapy selection switch interrupts flow to the Phasitron® venturi jet orifice, oscillation ceases with the total systemic flow directed through balance orifice 9B into the nebulizer inlet 9A causing an increase in the nebulization pressure, which increases the rate of aerosolization. When the therapy selection switch is moved to the Bi-Phasic™ IPV® position the oscillation circuit is reactivated which reduces the systemic pressure to the nebulizer (slightly reducing the nebulizer output) while re-activating the venturi jet sub tidal volume deliveries.

The initiating resistance to Phasitron® jet orifice inflow through the therapy selection switch 5 creates a gradual initiating sub tidal volume delivery, preventing an initial hard endobronchial impaction during the injection of the intrapulmonary sub tidal volume.

The following data provides for an improved understanding of the novel patient controlled Bi-Phasic™ percussive amplitude intervals:

1. The mode switch orifice restricts the ambient venting of the Phasitron® venturi jet orifice bleed air to ambient. When mode switch 11C is open (not depressed) the flow of air to the venturi and nebulizer jet orifices is decreased, creating a decrease in sub tidal delivery amplitude.
2. 
3. Peak percussive impaction amplitudes (for peripheral airway lung recruitment) are generated by not bleeding the Phasitron® jet orifice air to ambient, during sub tidal endobronchial deliveries.
4. An approximate 48 inch interfacing tubing receives (pulsatile) sub tidal volumes of air from the Phasitron® Service socket delivering into the Phasitron® venturi jet orifice. The Phasitron® inlet Tee piece is interconnected to the mode switch orifice 8A in FIG. 1. The mode switch orifice 11D meters bleed air-flow to ambient through the normally open mode switch 11C.
5. The initiating nebulizer power interfacing tubing connects into the Aerosol Service socket. The other end of the nebulizer interfacing tubing interconnects into the Aerosol Power Port 9A.
6. By depressing the mode switch button the patient can interrupt bleed air through the mode switch orifice to ambient, increasing the pressure to both the venturi and nebulizer jet orifices. This increases the sub tidal delivery amplitudes while concomitantly increasing nebulizer jet orifice flow.
6. Percussive impaction rates and associated amplitudes can be factory calibrated up or down, within clinical limits, by calibrating the Balance Orifice controlling nebulizer jet orifice flow.
7. The "Bi-Phasic™ Percussion" time metering valve control knob Arrow, allows the manual selection of cyclic sub tidal volume delivery rates. Control knob labeling consists of EASY 7B which means a rapid low amplitude sub tidal volume delivery, HARD 7C which means a lengthened, high amplitude sub tidal volume delivery and AVERAGE which can mean a clinically effective sub tidal volume delivery.
8. The (airway-interfacing device) Phasitron® venturi air injection velocities are sufficiently high at any cycling rate selection (with a circular mouth piece diameter) to direct a conic sub tidal volume injection into the physiological airways reducing the lip pressure required to essentially seal the mouthpiece with the lips, to minimize physiological ambient leakage.
9. Clinically the patient is allowed to manually schedule therapeutically effective percussive amplitudes, to mobilize and recruit the peripheral pulmonary airways with a Bi-Phasic™ sub tidal mandated minimal and maximal impaction.
10. For neonatal use and patient initiation only, the Bi-Phasic™ percussive amplitude can be reduced to lower impaction levels by manually removing the pressure monitoring plug (spoiler) near the outlet port of the Phasitron® respirator interface.
11. A bracket stored within the right facing travel pack pocket when installed, allows the patient positioning means for the breathing head.
12. Therefore, with manual thumb control over the Bi-Phasic™ mode switch the patient has total single thumb (optional) control over the mobilization and recruitment of the Bronchial airway caliber as well as, the clearance of mobilized peripheral airway secretions. This is accomplished by employing a manual controlled Bi-Phasic™ oscillatory lung percussion to mobilize and recruit the airways without manipulation of several other traditional control media.

Review of Applied Technology

An air compressor pack weighing some one-quarter of the existing heavy Impulsator® air compressor providing for effective repetitive oscillatory higher velocity percussive sub tidal volume injections required for percussive IPV® required the following innovations:

1. By using a much smaller compressional piston area with an adjusted stroke, requiring much less motivational motor force during the compressional upstroke, to generate operational demand pressures with a lesser stroke volume at higher delivery frequencies a novel IPV® apparatus was created. In comparison, the heavy Impulsator® uses a low rpm (large piston) high mass weight (about 18 pound) compressed air source to provide sufficient pneumatic energy for IPV® versus the high RPM (small piston) air compressor, with a low mass weight of about (6.5 pounds).
2. Increasing the rate of compressional strokes in a unit of time creates a ratio between the maximum expected endobronchial sub tidal delivery rate and the number of compression strokes per minute. For example; with the delivery of 500 sub tidal volumes per minute divided into the number of compression strokes of up to about 3500 strokes per minute, there would be about seven (7) air compression strokes for each sub tidal volume injected into the patient's pulmonary airways, at the maximum anticipated pulmonary sub tidal volume delivery rate of 500-650 cycles per minute. Each up stroke produces a millisecond "energy spike" which is transported into the airways of the lungs to assist in pulmonary airway inflation during the sub tidal volume deliveries.

The current (state of the art) heavy IMPULSATOR® air compressor uses a substantial piston area creating a higher stroke compression volume then necessary for the required air generating demand mandating higher power demand and mass than necessary for the application.

With novel comprehensive applications of technology innovating an existing IPV® apparatus a much reduced compressional air volume demand can be satisfied by an air compressor with considerably less piston area (reducing stroke volumes) by increasing the rate of compressional stroke volume deliveries required to satisfy the operational pneumatic energy demands for an effective Intrapulmonary Percussive Ventilation IPV®.

Each percussive endobronchial sub tidal volume delivery serves as an intrapulmonary transmission vehicle to be modulated by the micro compressional "energy spikes" (shock waves), created by each compressive piston upstroke. Thus the greater the rate of compressive stroke volume injections the greater the potential for endobronchial wall "micro agitation".

An increased temperature created by friction and air compression serves to near sterilize the compressed air. As the frictionally heated compressed air rapidly cools beyond the outlet of the oscillator cartridge, the near sterile water condensation is vented predominantly through the venturi jet orifice partially humidifying the endobronchial sub tidal volume deliveries.

Thus, the thermodynamic control over the internal heat dissipation (compressor cooling), is designed to prevent water condensation within the Oscillator cartridge and associated flow-timing components.

Percussive sub tidal volumes are further augmented by modifying the effective (airway-interfacing device) Phasitron® venturi flow-pressure entrainment ratios by increasing the velocity and volume of flow from the venturi jet orifice through the venturi aspirational throat geometry.

By computing the maximum required compressed air volume requirements with a functional oscillatory band width of from about 100 to 500, intra-airway sub tidal injection strokes per minute, will create i/e ratios of about 1:2.5 which will require the maintenance of operational pressures of from 30 to 35 psi.

The continuous mandated systemic flow, pressure, volume air generation for repetitive endobronchial percussive sub tidal volume injections, can be controlled by balancing any excess compressor generated air volumes through the nebulizer aerosol generating jet orifice.

The nebulizer is capable of generating therapeutic aerosol volumes far beyond that required for peripheral lung particulate deposition. Thus, the variations in excessive delivery of aerosol beyond optimal endobronchial airway requirements are used to balance the systemic operational pressures are of little, if any clinical consequence.

By balancing the augmentation of compressed air generation, a lesser air compressor output complies with the design of a lighter-weight miniaturized mobile Intrapulmonary Percussive Ventilation (IPV®) apparatus, thus by decreasing the weight while maintaining the clinical efficacy of IPV®, the logistical stress imposed upon semi invalid patient's with chronic and acute cardiopulmonary diseases is ameliorated.

Patient operational ease while providing increased clinical efficacy is increased by (aa) The elimination of a pressure reduction regulator and pressure monitoring gauge; (bb) operational flow and pressures do not have to be repeatedly adjusted by the patient to mobilize and then recruit endobronchial secretions, thus increasing operational ease; (cc) clinical nebulization pressures are automatically regulated by the patient's Bi-Phasic™ thumb control over the percussive amplitude during sub tidal volume deliveries. Patient control is present during both airway recruitment and airway secretion clearance; (dd) manometric monitoring of the patient's proximal airway pressures are eliminated, serving no therapeutic usefulness; (ee) the selection of percussive frequency band-width by the rotation of the (only patient access) time metering control knob 7A in FIG. 6 and FIG. 1 enables the patient or clinician to generally conform to the initiating size and severity of the patient's lung disease; (ff) when the breathing head (normally open) mode switch is ambient vented, the amplitude of the injected sub tidal volumes will be decreased. By applying thumb pressure to the mode switch 11C in FIG. 1 the sub tidal volume amplitude is increased for peripheral lung recruitment.

All of the above considerations allow unitized packaging shown in FIGS. 3, 4 with the following benefits, over current state of the art containment.

1. The unitized housing (box) packaging can encapsulate the air compressor and oscillatory IPV® components as well as, control access within a semi closed sound reduction compartment complemented by ambient access and vented cooling circulation.
2. The top cover panel of the encapsulated compartment can support the electrical ON-OFF switch, providing for terminated grounding with dual fused circuitry, assuring compressor power demand protection.

Access to "PERCUSSIVE" programming configuration and breathing circuit interfacing is enabled by:

1. Two outlet Service sockets provide for Bi-Phasic™ percussion and concomitant nebulization interfacing.
2. A two position switch labeled Therapy Selection with two directional throws, labeled "AEROSOL ONLY" and Bi-Phasic™ IPV® can be employed to produce a dense therapeutic aerosol, without percussive sub tidal volume delivery and/or sub tidal volume injection with aerosol.
3. Alternative dense aerosol alone can be programmed by interrupting the pulsatile air flow to the venturi jet orifice inlet 11A in FIG. 1.
4. The Remote and gauge service sockets are removed in the Home Therapy HT™ Impulsator®. Percussionator® greatly simplifying the airway-interfacing to the remote Phasitron®. Two of the Phasitron® interfacing tubing's to the servoing device are removed thus simplifying and increasing the patient's operational ease in setting up the Breathing Head assembly. Additionally, the two remaining interfacing tubings can be webbed creating a single tubing with two channels. The end fittings can be color coded to assure proper Service socket interconnections. Thus a two-channel web tubing can be used to interface the (airway-interfacing device) PHASITRON® and "NEBULIZATION" Service sockets.
5. The encapsulating unitized container (box) can be inserted within a typical weather resistant, padded, soft airline type travel bag 12 C in FIG. 4 to provide additional compressor noise obtunding, shock resistance if dropped, travel ease and the obscuration of medical device transport.
6. The typical encapsulating travel pack can have pockets on three sides with an inclusive cover.
7. One end side pocket can contain the electrical power cord, which is connected to the power switch through a grommet penetrating the inside wall of the fabric case and the wall of the device container, with cord pull out protection.
8. Ambient air conditioning of the basic device container provides for cooler ambient air entrainment and reverse ambient venting, through the aft wall of the box container and encapsulating travel pack.
9. The front facing pocket of the travel pack can accommodate the interfacing harnesses and medications.
10. A semi transparent pocket within the "flap cover" of the soft travel pack can maintain the printed operational manuals.
11. The opposing travel pack end compartment can accommodate the airway-interfacing Phasitron® and nebulizer breathing head components.

12. An (airway-interfacing device) Phasitron® Duo™ breathing head is interchangeable with the standard Phasitron® breathing head.

The encapsulated Intrapulmonary Percussive Ventilation IPV® therapy apparatus can be used within the institution, home or during vehicular travel when powered by direct ac 50 or 60 cycle and/or dc to ac power conversion; by a patient owner, professional institutional clinician administering to institutional patients, emergency medical team (EMT) etc. for mass cardiopulmonary casualty or localized respiratory care treatments.

Additionally the deep drawn aluminum housing containing the IPV® apparatus can be used free standing without the travel case encapsulation.

Figure 9A:
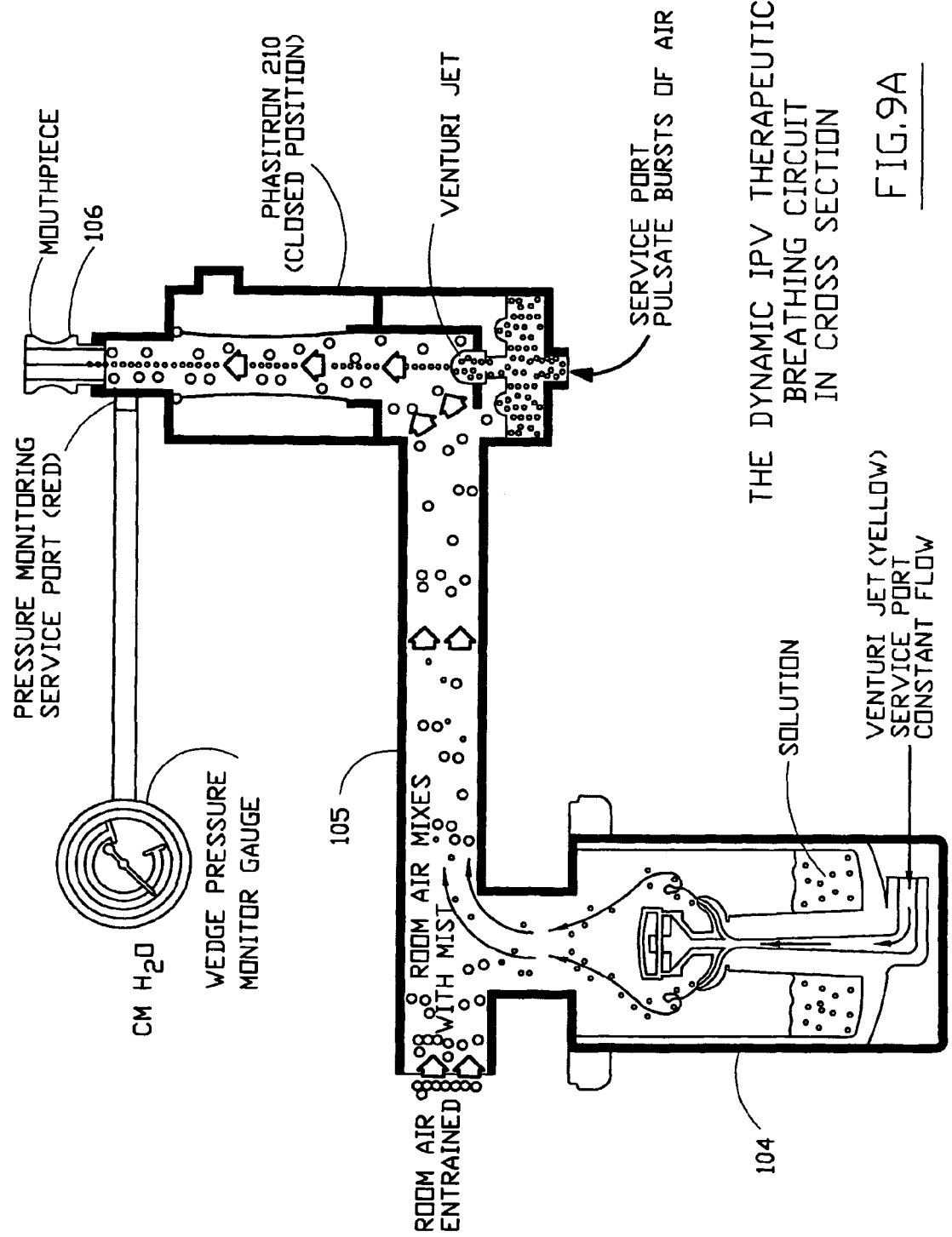

FIG. 9A shows the dynamic IPV therapeutic breathing circuit. Nebulizer 104 is fed a constant flow of gas into the inlet of the venturi port. Solution in the nebulizer 104 is converted into mist which mist is then mixed at junction 105 with room air. The service port (labeled white) leads to another venturi jet and then the activated mist is passed through the Phasitron valving system 210 to mouthpiece 106. A pressure monitoring port (labeled red) may lead to a wedge pressure monitor gauge.

Figure 9B:
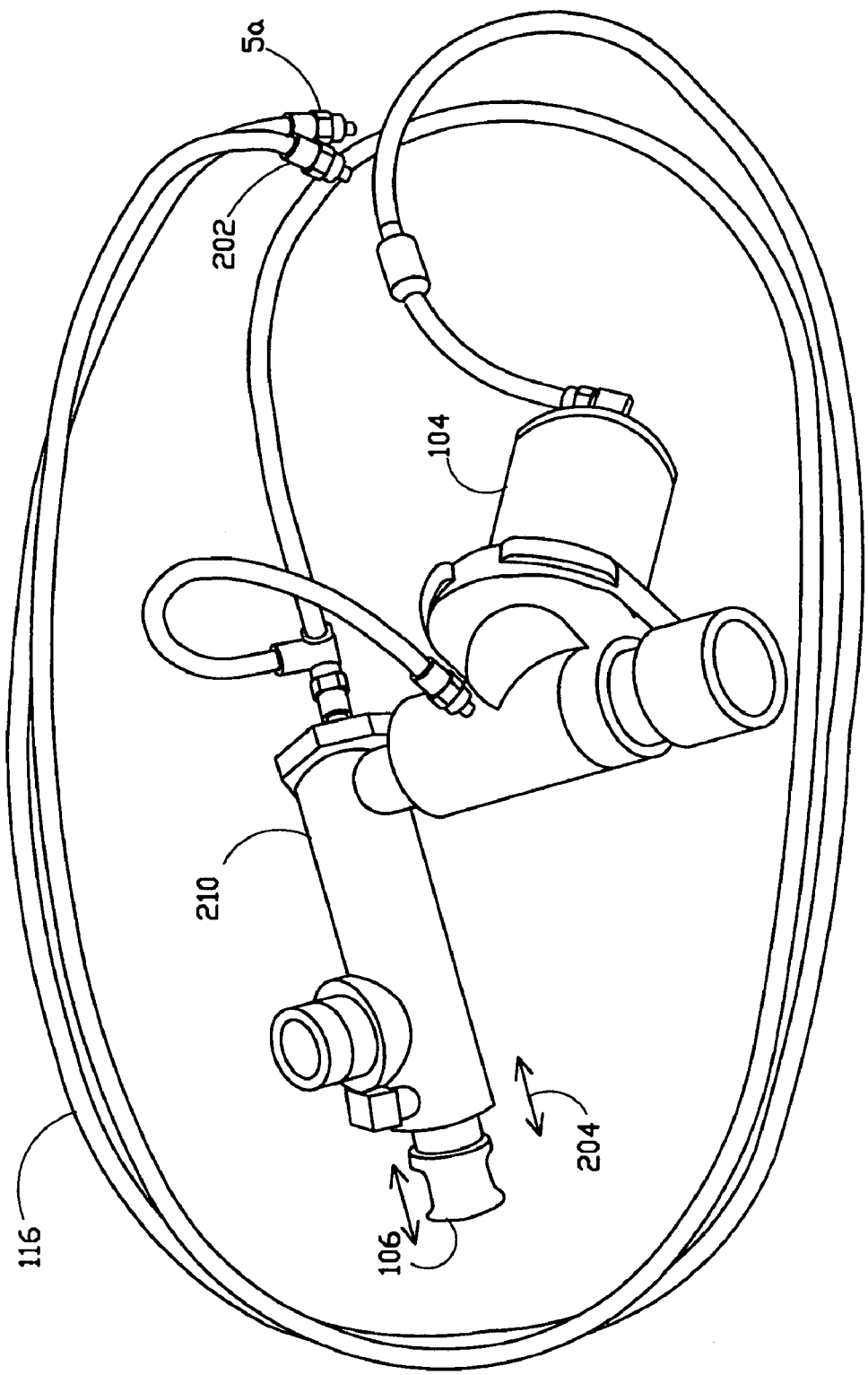

FIG. 9B is a standard Home Therapy HT™ Impulsator® breathing circuit for connecting to facemasks and indwelling physiological airways as well as, patient mouthpieces 106. Arrow 204 shows mouthpiece removal. The separate universal nebulizer 104 and Phasitron® valving system 210 with a failsafe ambient venting sleeve valve is employed for neonatal, pediatric and adult institutional cardiopulmonary patient use. The Figure shows a separate but interconnected Phasitron® 210 with a physical-physiological interface. Further, the interfacing tubing 11b (typically consisting of a 48" tube) has connection ports or fixtures 202, 5a, a yellow Nebulizer connection port 202 and white Phasitron® connection port 5a, with interconnections on one end, with Home Therapy HT™ Impulsator yellow Nebulizer and white Bronchotron® service sockets on the opposing end.

Figure 9C:
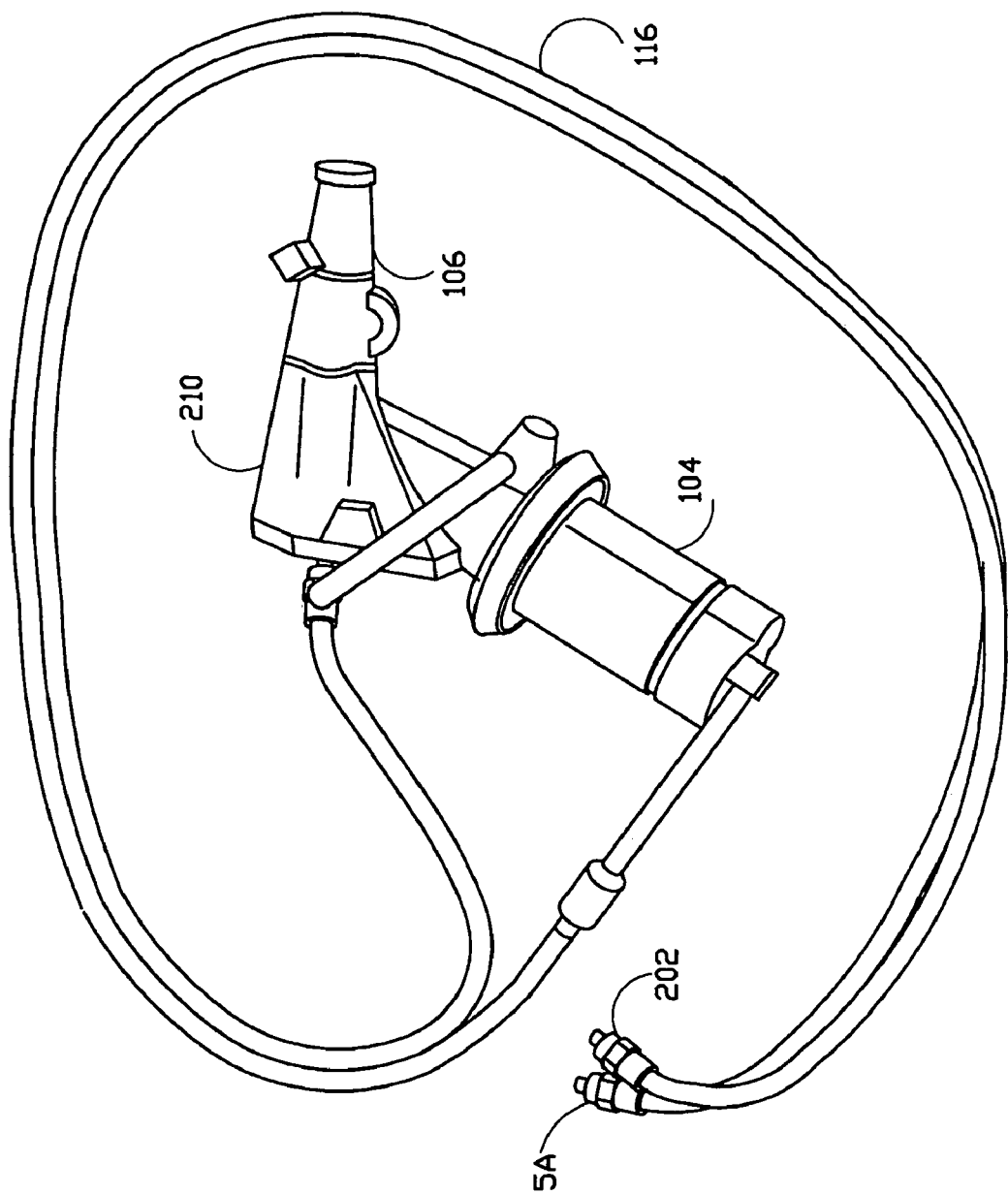

FIG. 9C shows an alternative Phasitron Duo™ breathing head with fixed mouth piece 106 for cooperative long term Home Care COPD and/or chronic cardiopulmonary patient therapy. The nebulizer 104 is conjoined with the Phasitron® valving system 210 for cooperative patient Cardiopulmonary patient use. Further, the unit has a separate interconnected Phasitron® physical-physiological interface. This alternative head system has interfacing tubing 116 (typically 48") with connection ports or fixtures 202, 5a, that is, a yellow nebulizer connection port 202 and white Phasitron® connection port 5a on one end, and with interconnection ports for the Home Therapy HT™ Impulsator yellow nebulizer and white Bronchotron® service sockets on the opposing end.

The following is a discussion relating to the Home Therapy HT™ Impulsator® breathing circuits. The breathing circuit differs substantially from the standard mono IPV® breathing circuits in the following three manners.

First, they only use two (2) interfacing tubing connections as opposed to four (4) on the existing mono IPV® breathing circuits. Second, the Phasitron sliding venturi modulates the delivery of the scheduled repetitive intrapulmonary sub tidal volumes with higher frequency amplified compressional stroke energy bursts, to mechanically increase the inspiratory inflational elastomeric yield of the transporting bronchiolar airway walls, which serves to enhance their associated intrathoracic intravascular pulsatile blood flows as well as directional passive lymphatic fluidic flows. This intrapulmonary sub tidal volume with higher frequency amplified compressional stroke energy bursts was not previously available.

Third, the higher frequency percussive amplitudes of the manually scheduled Bi-Phasic™ pulsatile endobronchially delivered sub tidal volume are scheduled by the patient depressing or relaxing digital (thumb or finger) pressure upon a pneumatic Bi-Phasic™ impulse amplitude switch. This manual percussive amplitude control by the patient enables the patient to manually control a sinusoidal amplitude of the scheduled higher frequency tidal volume deliveries to produce a balanced intrapulmonary gas exchange. This manual control of the sinusoidal amplitude enables the patient to increase their oxygen uptake with less tidal delivery amplitude as well as "blow off" $CO_2$ with higher amplitude sub tidal deliveries, while maintaining the same sub tidal delivery frequencies.

Total sub tidal amplitude control by patient thumb is activated switching over Bi-phasic amplitude during active IPV® therapy has not been employed previously by prior art devices.

The claims appended hereto are meant to cover modifications and changes within the scope and spirit of the present invention.

What is claimed is:

1. A method for ventilating a patient airway during the inspiratory phase and expiratory phase from a source of gas under pressure from a compressor comprising:
   supplying to the patient airway during the inspiratory phase a plurality of pulses of small volumes of gas from said source of gas, said pulses representing positive pressure endobronchial sub total volumes,
   adding in succession the plurality of pulses of small volumes of gas to provide successively greater volumes of gas successively increasing in pulsatile form the pressure of the gas in the airway of the patient during the inspiratory phase by adding the successively greater volumes of gas in the airway of the patient being caused solely by the successive addition of the plurality of pulses of small volumes of gas and serving to provide diffusive ventilation to the patient during the inspiratory phase, and, permitting the patient to exhale during the expiratory phase;
   distributing high frequency compressor generated energy spikes created during stroke volume generation, into a distribution system serving as an accumulator in preparation for the energy spikes to be transported into the lungs, wherein said distribution system comprises a primary venturi body with a jet orifice and a nebulizer with a jet orifice; and,
   balancing an endobronchial sub tidal pressure gradient with two outflow orifices serving to create a pressure-volume regulated operational air flow into the primary venturi jet orifice with pressure rise balancing by secondary flow through the jet orifice of the nebulizer.

2. A method for ventilating a patient airway as in claim 1 including manually selecting separate peripheral pulmonary airway mobilization and recruitment amplitudes and oscillatory frequencies for respective aerosol delivery methods during active lung therapy.

3. A method for ventilating a patient airway as in claim 2 wherein
   said manually selecting includes manually selecting and manipulating a manual bi-phasic switch controlled orifice.

4. A method for ventilating a patient airway as in claim 2 wherein
   the manually selecting separate peripheral pulmonary airway mobilization and recruitment amplitudes and oscillatory frequencies controls two clinical modalities:

a percussive oscillation commenced by allowing ambient venting, and an oscillatory bi-phasic amplitude supply of air to the patient's airway causing mobilization or recruitment of the patient's lungs by obstructing or occluding ambient venting.

5. A method for ventilating a patient airway as in claim 1 including muting sub tidal volume delivery with a two-position or bi-modal switch representing "bi-phasic operation" or "nebulization only" operation.

6. A method for ventilating a patient airway as in claim 1 including automating optimal operational pressures for different patients due to their physical size and therapeutic requirements without an operational pressure monitoring gauge.

7. A method for ventilating a patient airway as in claim 1 including allowing the patient to select a clinically effective pulmonary airway mobilization and recruitment program without operational pressure manipulation, thereby eliminating a breathing pressure manometer.

8. A method for ventilating a patient airway as in claim 1 including providing a continuous mandatory ventilation (CMV) ventilator, wherein a percussive diffusive wave format is supplied to a host convective volume-pressure oriented CMV ventilator.

9. A method for ventilating a patient airway as in claim 1 wherein the method includes amplifying the air supply from said compressor to create a constant air supply to percuss the lungs with sufficient therapeutic amplitude to mobilize and recruit the peripheral airways with intrapulmonary percussive ventilation, and maintaining compressed air from said compressor to power said nebulizer with a particulate spectrum and volume.

10. A method for ventilating a patient airway as in claim 9 including balancing the total compressor outflow to provide sufficient percussive amplitude and concomitant nebulization over a selectable frequency band.

11. A method for ventilating a patient airway as in claim 9 wherein the compressor includes a piston and the method including employing compressional shock waves created during repetitive compressive upstrokes of the air compressor piston which serve to modulate the positive pressure endobronchial sub tidal volume deliveries with energy spikes.

12. A method for ventilating a patient airway as in claim 11 wherein 3500 compressional shock waves are employed.

13. A method for ventilating a patient airway as in claim 9 including providing a luggage case with a soft padded interior for said compressor;

venting said case for augmented ambient air flow there through for compressor cooling.

14. A method for ventilating a patient airway as in claim 13 wherein said luggage case has interior side walls, the method including storing therapeutic breathing head components and medications about said side walls and storing an inter connected power cord for said compressor in said luggage case.

15. A method for ventilating a patient airway as in claim 13 including buffering compressor noise during operation of said compressor.

16. A method for ventilating a patient airway as in claim 13 including absorbing force shock when said luggage storing said compressor is dropped from an elevation.

17. A method for ventilating a patient airway as in claim 16 wherein the absorption of said shock force includes absorption of shock force in excess of a vertical drop by a patient from a patient's hip-level to a hard surface.

18. A method for ventilating a patient airway as in claim 13 including opening said luggage to expose a control panel including one or more of a compressor start and stop switch, percussion frequency band selection and breathing head service sockets.

19. A method for ventilating a patient airway as in claim 18 including providing a control panel with controls for said adding in succession the plurality of pulses of small volumes of gas;

covering said control panel with a flip over fabric cover to conceal said control panel, said fabric cover impervious to medication spills.

20. A method for ventilating a patient airway as in claim 19 including physically separating said luggage from said compressor and controls and control panel thereby said compressor and controls and control panel can provide stand-alone therapy apart from said luggage.

21. A method for ventilating a patient airway as in claim 18 including providing fringe access for interconnecting a breathing head tubing while substantially simultaneously muting compressor noise during operation thereof.

22. A method for ventilating a patient airway as in claim 18 wherein said compressor is supplied with ac power for operation, the method including converting dc power into ac power for said compressor, and providing an interconnection for said ac power source.

23. A method for ventilating a patient airway as in claim 1 including producing endobronchial shock waves with vibratory ratio of about seven modulating shock waves during each endobronchial sub tidal volume injection.

24. A method for ventilating a patient airway as in claim 23, wherein the ratio of about seven modulating shock waves involves delivery of 500 sub tidal volumes per minute divided into the number of compression strokes of up to about 3500 strokes per minute, resulting in about seven air compression strokes for each sub tidal volume injected into the patient's pulmonary airways.

25. A method for ventilating a patient airway as in claim 23 wherein producing endobronchial shock waves creates endobronchial micro agitation which causes the walls of the pulmonary airways to be more compliable to volume change.

26. A method for ventilating a patient airway as in claim 1 including gradually initiating sub tidal volume delivery, thus preventing an initial hard endobronchial impaction.

27. A method for ventilating a patient airway as in claim 1 including regulating, within a predetermined delivery pressure variance range, injection of the sub tidal volumes into the patient's airways.

28. A method for ventilating a patient airway as in claim 1 including wherein the compressor stroke energy spikes, transmitted through the primary venturi jet orifice form micro energy spikes adapted to impact upon elastomeric walls of physiological pulmonary airways of the patient's airways, thereby adapted to create an expansive dilating force during a period of a transient pressure rise causing a sub tidal airway inflation.

29. A method for ventilating a patient airway as in claim 28 including
providing the nebulizer jet orifice adapted to convert a liquid into an aerosol with a designed particulate spectrum within a predetermined nebulizer jet orifice pressure variance, such that the constant flow to the nebulizer jet orifice will vary during inspiratory endobronchial sub tidal volume injection and follow on to an expiratory, no-flow period.

30. A method for ventilating a patient airway as in claim 29 including
providing a variable jet orifice flow to regulate or buffer an operational pressure within an operational therapeutic pressure range.

31. A method for ventilating a patient airway as in claim 30 including
creating scheduled pulsatile intrapulmonary sub tidal flows from the primary venturi jet orifice creates a periodic inflow pressure gradient serving to aspirate a volume of the particulate aerosol for concomitant aerosol delivery into the patient's airways.

32. A method for ventilating a patient airway as in claim 31 including
after the sub tidal delivery or expiratory interval, purging mechanical airways as part of nebulizer outflow before venting the outflow to ambient with mixed exhaled physiological gases from the patient's airways.

33. A method for ventilating a patient airway as in claim 32 including
providing a proximal non-gated venturi tube which is ambient vented allowing the compressible gases being delivered the patient's airways to obstructionally increase and decrease the primary venturi body pressures, in near instantaneous compliance with changing inflational endobronchial airway resistances.

34. A method for ventilating a patient airway as in claim 33 including
with a near constant primary jet orifice injection pressure, a constant inflational variance on resistances of the patient's airways which cause pressures of the primary venturi body created entrainment gradient to be influenced by the pulmonary airway resistance changes.

35. A method for ventilating a patient airway as in claim 28 including
governing an outflow velocity from the primary venturi body by an ever-changing inflational pulmonary endobronchial resistances to inflow.

36. A method for ventilating a patient airway as in claim 35 including
governing an outflow velocity of the primary venturi body by an ever-changing inflational pulmonary endobronchial resistances of the patient's airways to inflow, thereby limiting conversion of a constant inflow into the patient's airways due to an abrupt pressure rise within the patient's preferential bronchiolar airways.

37. A respirator for ventilating a patient's airway during the inspiratory phase and expiratory phase, said respirator being supplied with gas under pressure from a source of pressurized gas with a compressor, comprising:
means for supplying a plurality of pulses of small volumes of gas from said source of gas to the patient airway during the inspiratory phase,
means, coupled to said means for supplying, for adding successively greater volumes of gas pulses as part of said small pulses of gas, to provide successively greater volumes of gas, successively increasing in pulsatile form, the pressure of the gas in the airway of the patient during the inspiratory phase resulting in diffusive ventilation to the patient during the inspiratory phase, and,
means for distributing high frequency compressor generated energy spikes created during stroke volume generation, into a distribution system serving as an accumulator in preparation for the energy spikes to be transported into the lungs, wherein said distribution system comprises a primary venturi body with jet orifice and a nebulizer with jet orifice;
two outflow orifices configured to balance a endobronchial sub tidal pressure gradient by creating a pressure-volume regulated operational air flow into the primary venturi jet orifice with pressure rise balancing by secondary flow through the jet orifice of the nebulizer; and,
means for permitting the patient to exhale during the expiratory phase.

38. A respirator as claimed in claim 37 wherein the respirator includes:
means, coupled to said means for supplying, for generating a constant air supply to percuss the lungs by amplifying the air supply from said compressor, and
nebulizer maintaining a compressed air volume and particulate spectrum, said aerosol generator or nebulizer coupled to said means for supplying.

39. A respirator as claimed in claim 38:
including a frequency selector means for controlling percussive amplitude and nebulization, said frequency selector means coupled to said means for supplying.

40. A respirator as claimed in claim 37 including a manual bi-phasic switch for said means for supplying which controls amplitudes and oscillatory frequencies delivered to said nebulizer.

41. A respirator as claimed in claim 38 including:
a luggage case with a soft padded interior for said compressor;
a case vent permitting ambient air flow there through for said compressor,
said case having buffering walls limiting compressor noise and shock absorbing wall segments;
said respirator having control panel;
said luggage having a control panel opening with a fabric cover to conceal said control panel.

42. A respirator as claimed in claim 38 wherein the compressor includes a piston and said means for supplying employs compressional shock waves created during repetitive compressive upstrokes of the air compressor piston which serve to modulate a positive pressure endobronchial sub tidal volume deliveries with vibratory energy.

43. A respirator as claimed in claim 42 wherein said means for supplying produces endobronchial shock waves with vibratory ratio of about seven modulating shock waves during each endobronchial sub tidal volume injection.

44. A respirator as claimed in claim 37
wherein said respirator is a continuous mandatory ventilation (CMV) ventilator, and
said means for supplying includes means for generating a percussive diffusive pressure air waves supplied to a host convective volume-pressure oriented CMV ventilator.

* * * * *